(12) United States Patent
Tanaka et al.

(10) Patent No.: US 11,369,626 B2
(45) Date of Patent: Jun. 28, 2022

(54) THERAPEUTIC AGENT FOR NERVOUS SYSTEM DISEASE

(71) Applicants: OSAKA UNIVERSITY, Suita (JP); NIPPON ZOKI PHARMACEUTICAL CO., LTD., Osaka (JP)

(72) Inventors: Hiroyuki Tanaka, Suita (JP); Hideki Yoshikawa, Suita (JP); Hideki Mochizuki, Suita (JP); Tsuyoshi Murase, Suita (JP); Tsutomu Sasaki, Suita (JP); Kousuke Baba, Suita (JP); Toru Iwahashi, Suita (JP); Mitsuru Naiki, Kato (JP)

(73) Assignees: OSAKA UNIVERSITY, Osaka (JP); NIPPON ZOKI PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 16/907,913

(22) Filed: Jun. 22, 2020

(65) Prior Publication Data
US 2021/0008092 A1 Jan. 14, 2021

Related U.S. Application Data

(63) Continuation of application No. PCT/JP2018/046945, filed on Dec. 20, 2018.

(30) Foreign Application Priority Data

Dec. 21, 2017 (JP) .............................. JP2017-245133
Aug. 23, 2018 (JP) .............................. JP2018-156503

(51) Int. Cl.
*A61K 31/714* (2006.01)
*A61P 25/28* (2006.01)
*A61K 9/00* (2006.01)

(52) U.S. Cl.
CPC .......... *A61K 31/714* (2013.01); *A61K 9/0019* (2013.01); *A61P 25/28* (2018.01)

(58) Field of Classification Search
None
See application file for complete search history.

(56) References Cited

U.S. PATENT DOCUMENTS

| 6,121,249 A * | 9/2000 | Weissman | A61K 45/06 |
| | | | 514/52 |
| 6,951,658 B1 * | 10/2005 | Pearson | A61K 9/0019 |
| | | | 424/283.1 |
| 2003/0018009 A1 * | 1/2003 | Collins | A23G 3/368 |
| | | | 514/52 |
| 2004/0157783 A1 * | 8/2004 | McCaddon | A61K 31/714 |
| | | | 514/52 |
| 2005/0032740 A1 * | 2/2005 | Venkataraman | A61K 31/714 |
| | | | 514/52 |
| 2007/0178141 A1 * | 8/2007 | Brown | A61K 9/007 |
| | | | 424/440 |
| 2008/0139498 A1 * | 6/2008 | Goerne | A61K 31/525 |
| | | | 514/52 |
| 2012/0207790 A1 | 8/2012 | Maruyama et al. | |
| 2013/0143812 A1 | 6/2013 | Kadowaki et al. | |
| 2014/0066397 A1 | 3/2014 | De Wilde et al. | |
| 2015/0335627 A1 | 11/2015 | Yue et al. | |
| 2016/0235786 A1 * | 8/2016 | Hughes | A61K 35/545 |
| 2019/0083415 A1 | 3/2019 | Tanaka et al. | |

FOREIGN PATENT DOCUMENTS

| CN | 1261535 A | 8/2000 | |
| CN | 102631667 A | 8/2012 | |
| CN | 102772407 A | 11/2012 | |
| CN | 104688763 A | 6/2015 | |
| CN | 107595874 A * | 1/2018 | .......... A61K 31/365 |
| JP | H 10218775 A * | 8/1998 | ............ A61B 19/00 |
| JP | 2014-511830 A | 5/2014 | |

(Continued)

OTHER PUBLICATIONS

Wiesmann, M., Zinnhardt, B., Reinhardt, D., Eligehausen, S., Wachsmuth, L., Hermann, S., . . . & Heerschap, A. (2017). A specific dietary intervention to restore brain structure and function after ischemic stroke. Theranostics, 7(2), 493. (Year: 2017).*

Disease definition, obtained from https://www.google.com/search on Nov. 10, 2020 (Year: 2020).*

Seiichi Ichimaru. "Attempt To Treat Dementia Patients With Cerebrovascular Disease By Megadose of Methyl B12". The Japanese Journal of Clinical and Experimental Medicine, vol. 66, No. 1, Jan. 1989, pp. 310-316.

Mar. 26, 2019 International Search Report issued in International Patent Application No. PCT/JP2018/046945.

(Continued)

*Primary Examiner* — Dale R Miller

(74) *Attorney, Agent, or Firm* — Oliff PLC

(57) ABSTRACT

A method of treating a central nervous system disease, the method including administering an agent including a therapeutically effective amount of vitamin $B_{12}$ to a patient with a central nervous system disease to treat the central nervous system disease. This disclosure also relates to a method of promoting M2 macrophage/microglia induction, inhibiting M1 macrophage/microglia induction, and/or reducing the ratio of M1 macrophage/microglia to M2 macrophage/microglia in a patient in need thereof, the method including administering an agent including a therapeutically effective amount of vitamin $B_{12}$ to the patient to promote M2 macrophage/microglia induction, inhibit M1 macrophage/microglia induction, and/or reduce the ratio of M1 macrophage/microglia to M2 macrophage/microglia. This disclosure also relates to a pharmaceutical product including vitamin $B_{12}$.

7 Claims, 17 Drawing Sheets

(56) References Cited

FOREIGN PATENT DOCUMENTS

| JP | 2016-513694 | A | 5/2016 | |
|---|---|---|---|---|
| WO | WO-2009071905 | A2 * | 6/2009 | ........... A61K 31/714 |
| WO | 2011/043136 | A1 | 4/2011 | |
| WO | 2011/149036 | A1 | 12/2011 | |
| WO | 2014/152504 | A1 | 9/2014 | |

OTHER PUBLICATIONS

Jun. 23, 2020 International Preliminary Report on Patentability issued in International Patent Application No. PCT/JP2018/046945.
Koji Suzuki et al. "Electrospun Nanofiber Sheets Incorporating Methylcobalamin Promotenerve Regeneration and Functional Recovery in a Rat Sciatic Nerve Crush Injury Model". Acta Biomaterialia, vol. 53, Apr. 15, 2017, pp. 250-259.
Tetsuya Watanabe et al. "Ultra-High Dose Methylcobalamin Promotes Nerve Regeneration in Experimental Acrylamide Neuropathy". Journal of the Neurological Sciences, vol. 122, issue 2, Apr. 1994, pp. 140-143.
Kazuto Yamazaki et al. "Methylcobalamin (Methyl-B12) Promotes Regeneration of Motor Nerve Terminals Degenerating in Anterior Gracile Muscle of Gracile Axonal Dystrophy (GAD) Mutant Mouse". Neuroscience Letters, vol. 170, No. 1, Mar. 28, 1994, pp. 195-197.
"Drug for Peripheral Neuropathies". Methycobal Tablets, Eisai Co., Ltd., Feb. 2014.
Seiichi Ichimaru. "Attempt To Treat Dementia Patients With Cerebrovascular Disease By Megadose of Methyl B12". The Japanese Journal of Clinical and Experimental Medicine, vol. 66, No. 1, January 2989, pp. 310-316.
Alessandro Pezzini et al. "Homocysteine and Cerebral Ischemia: Pathogenic and Therapeutic Implications". Current Medicinal Chemistry, vol. 14, No. 3, 2007, pp. 249-263.
Nov. 12, 2019 Office Action issued in Japanese Patent Application No. 2019-554940.
Jul. 30, 2021 Search Report issued in European Patent Application No. 18892293.4.

* cited by examiner

[Fig.1]
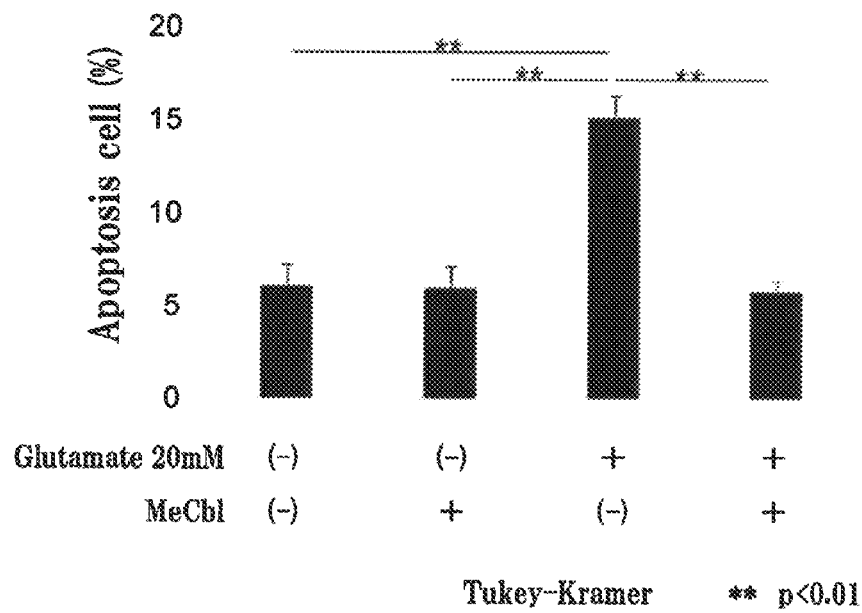
[Fig.2]
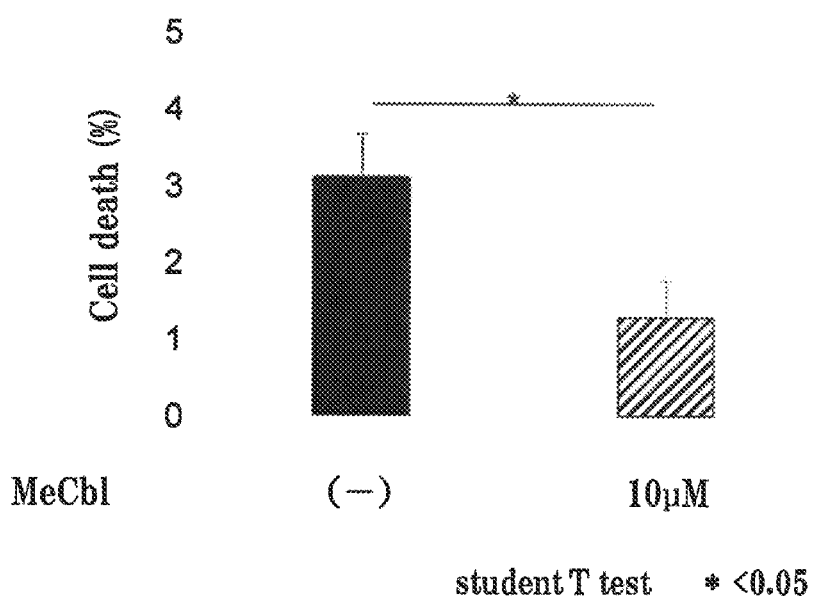

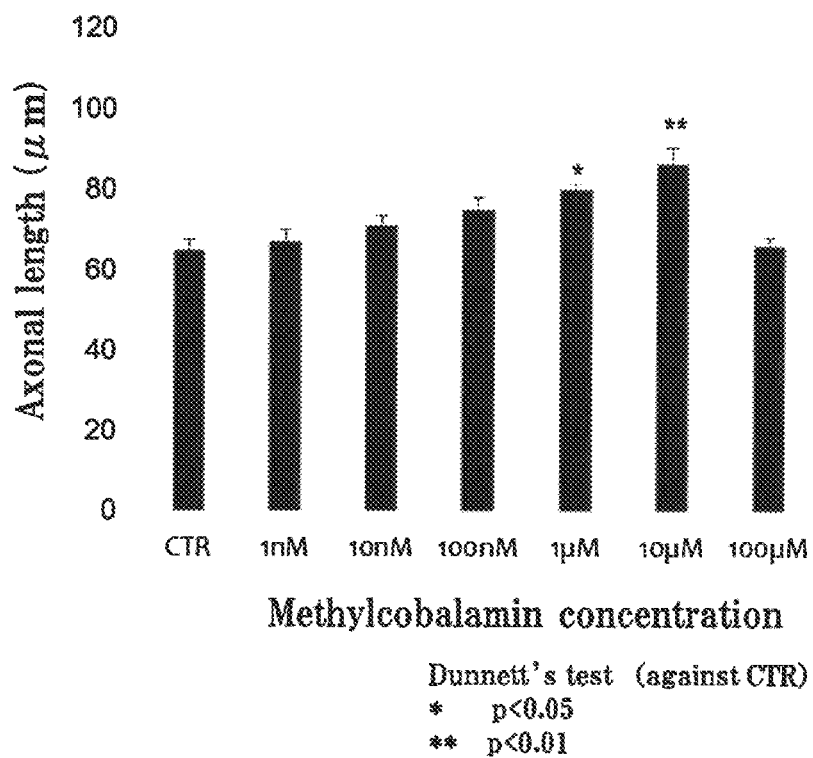
[Fig.3]
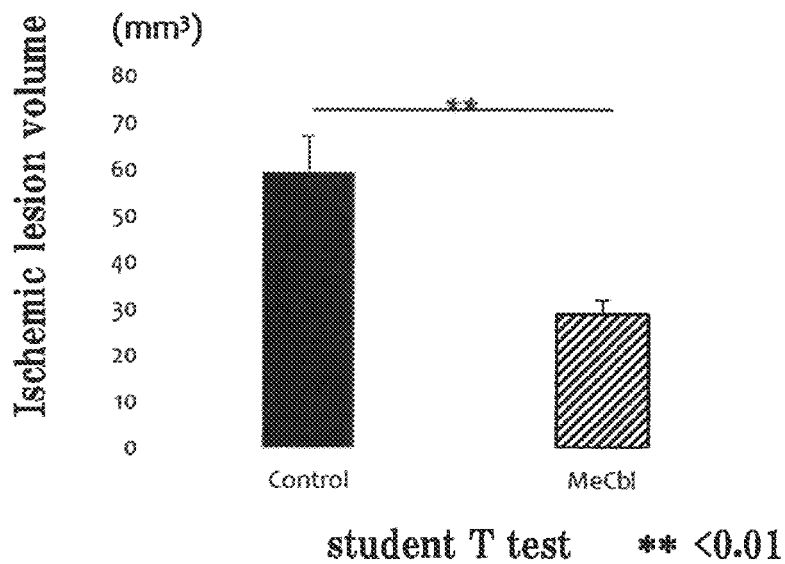
[Fig.4]

[Fig.5]
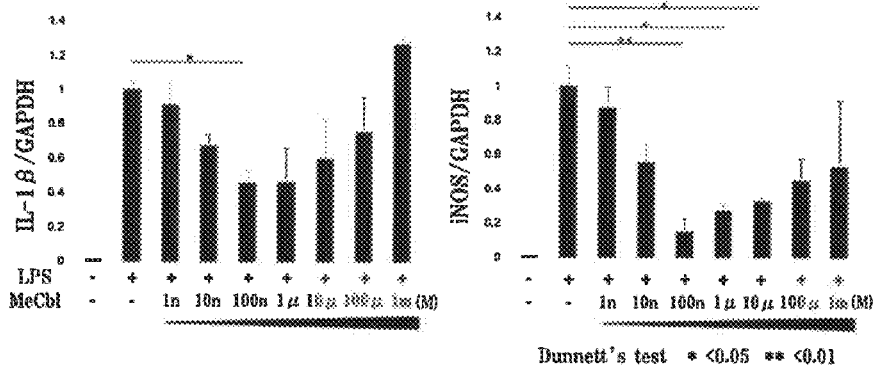
[Fig.6]
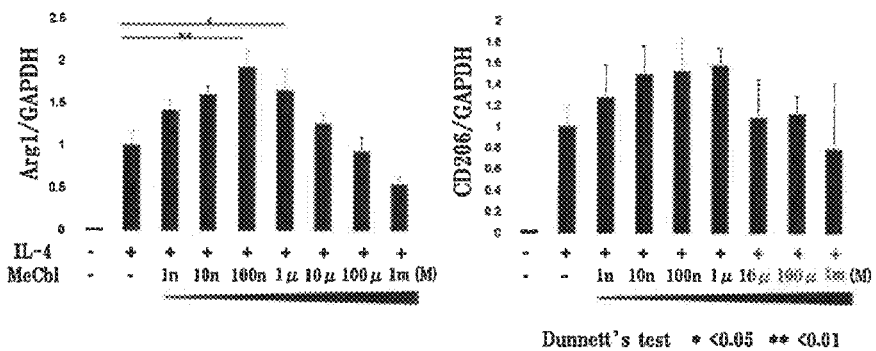
[Fig.7]
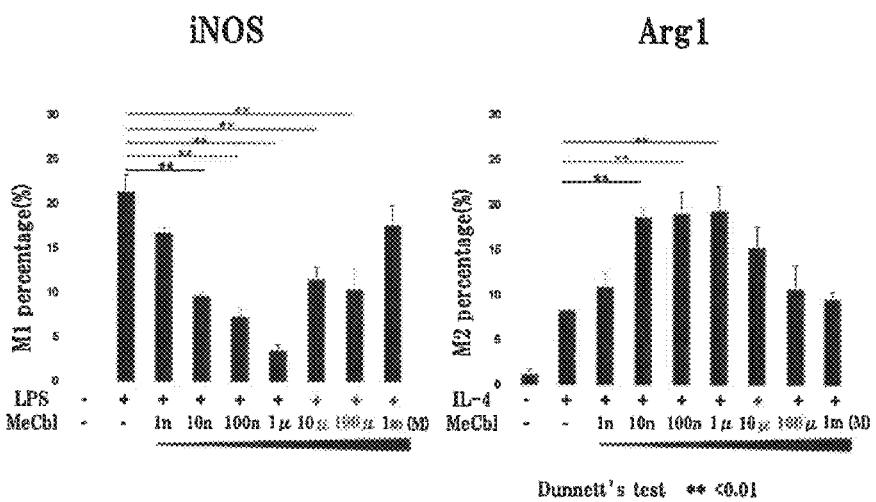

[Fig.8-1]
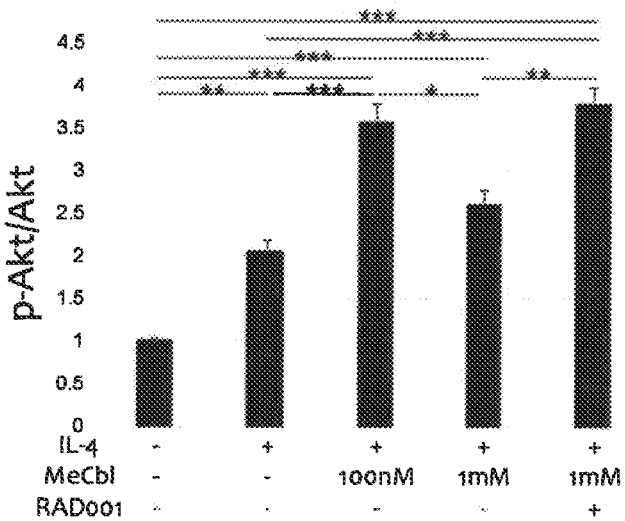
[Fig.8-2]
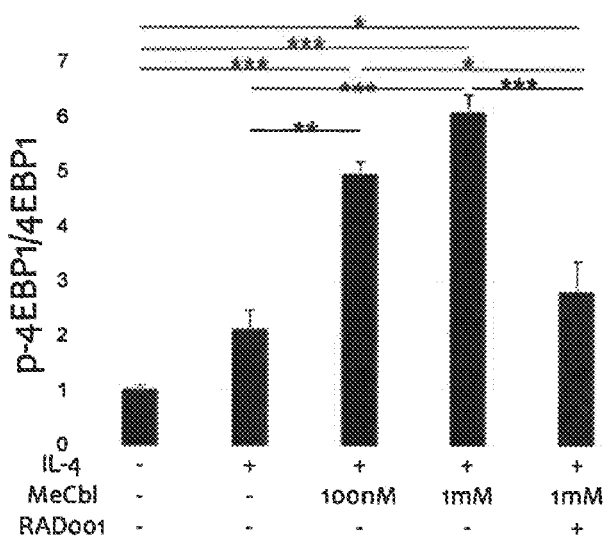

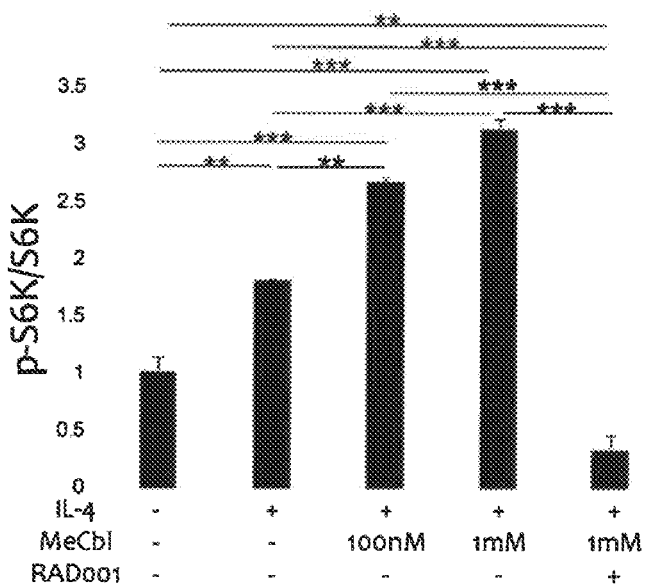
[Fig.8-3]

[Fig. 9]
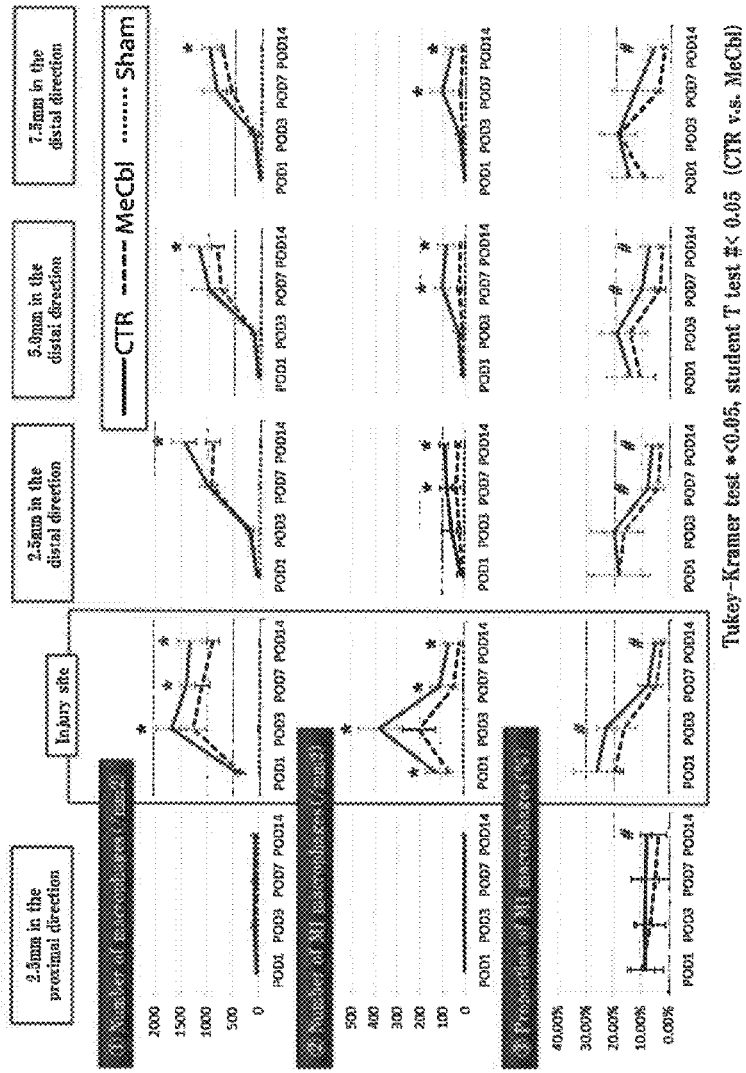

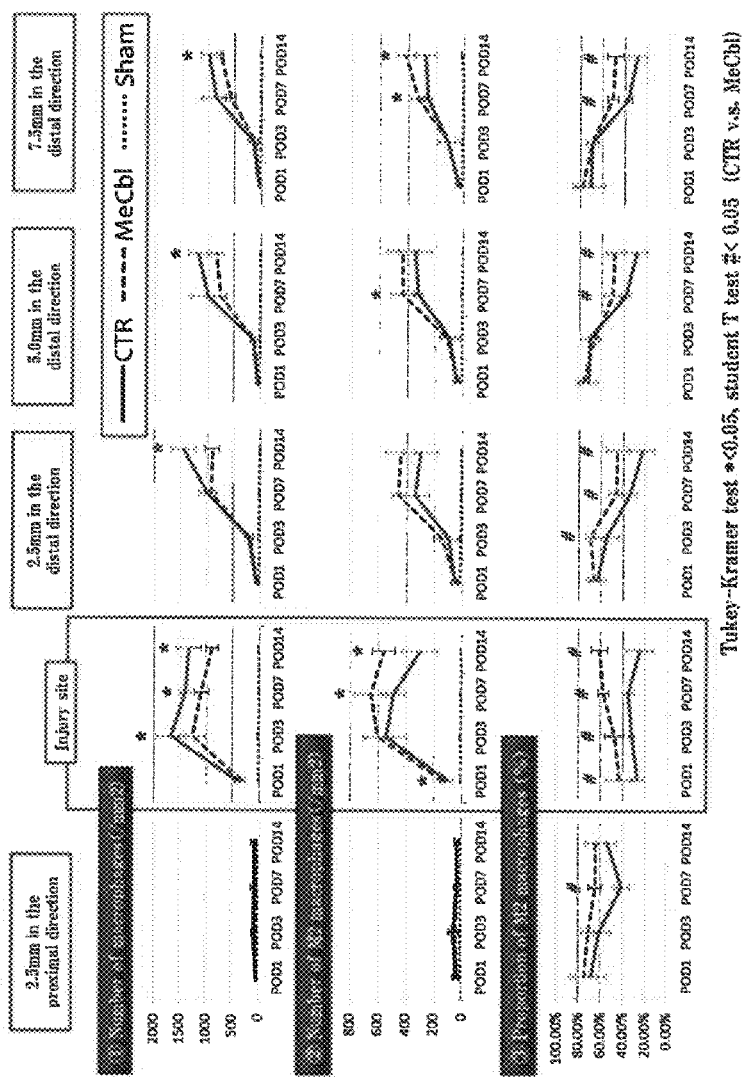
[Fig. 10]

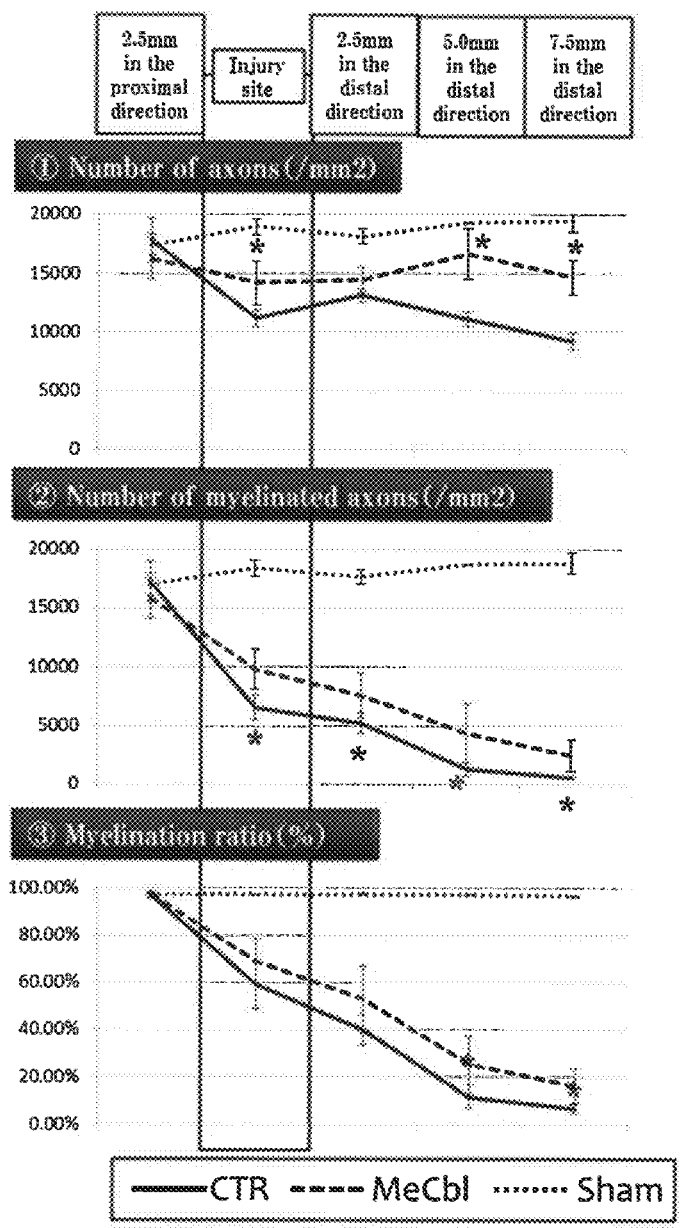

[Fig.12]
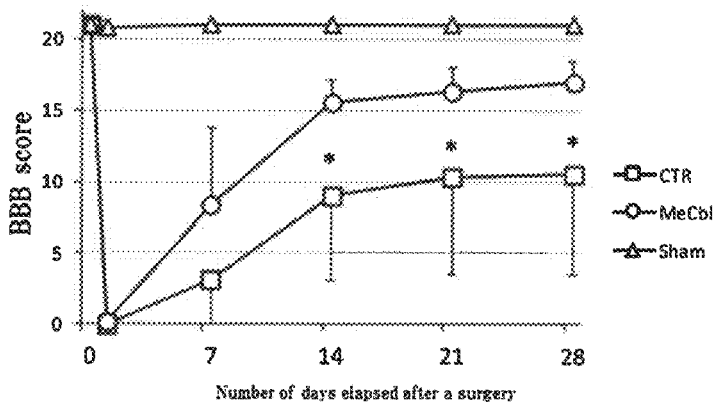
[Fig.13]
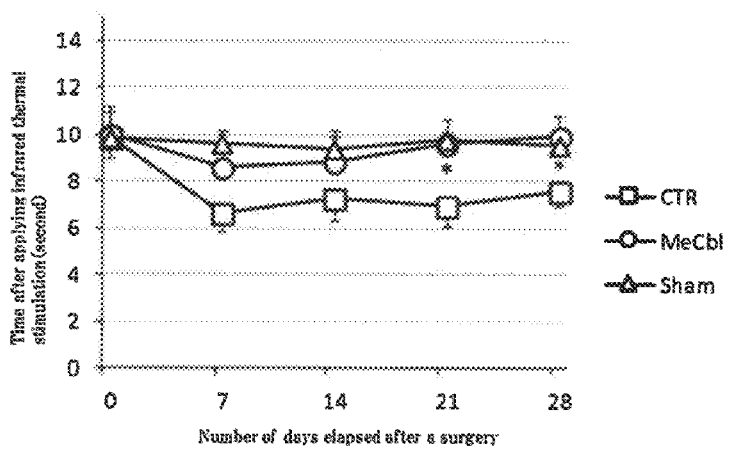
[Fig.14]
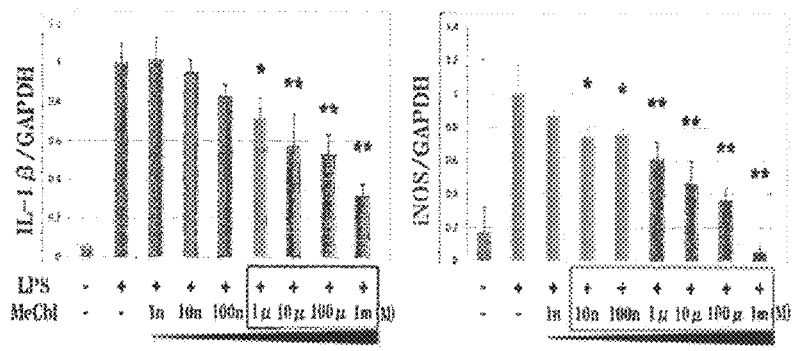

[Fig.15]
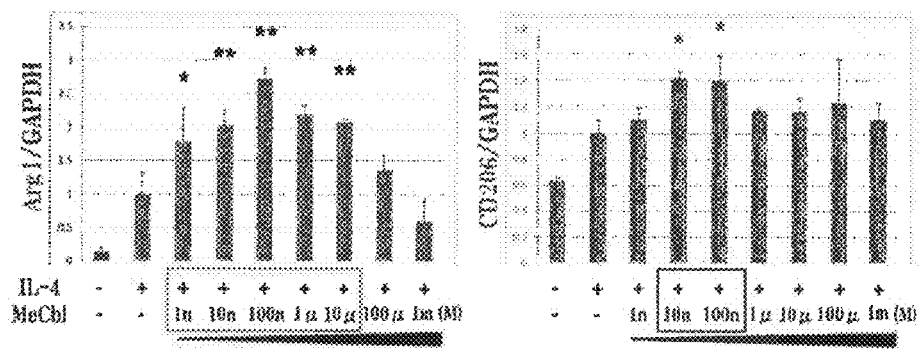
[Fig.16]
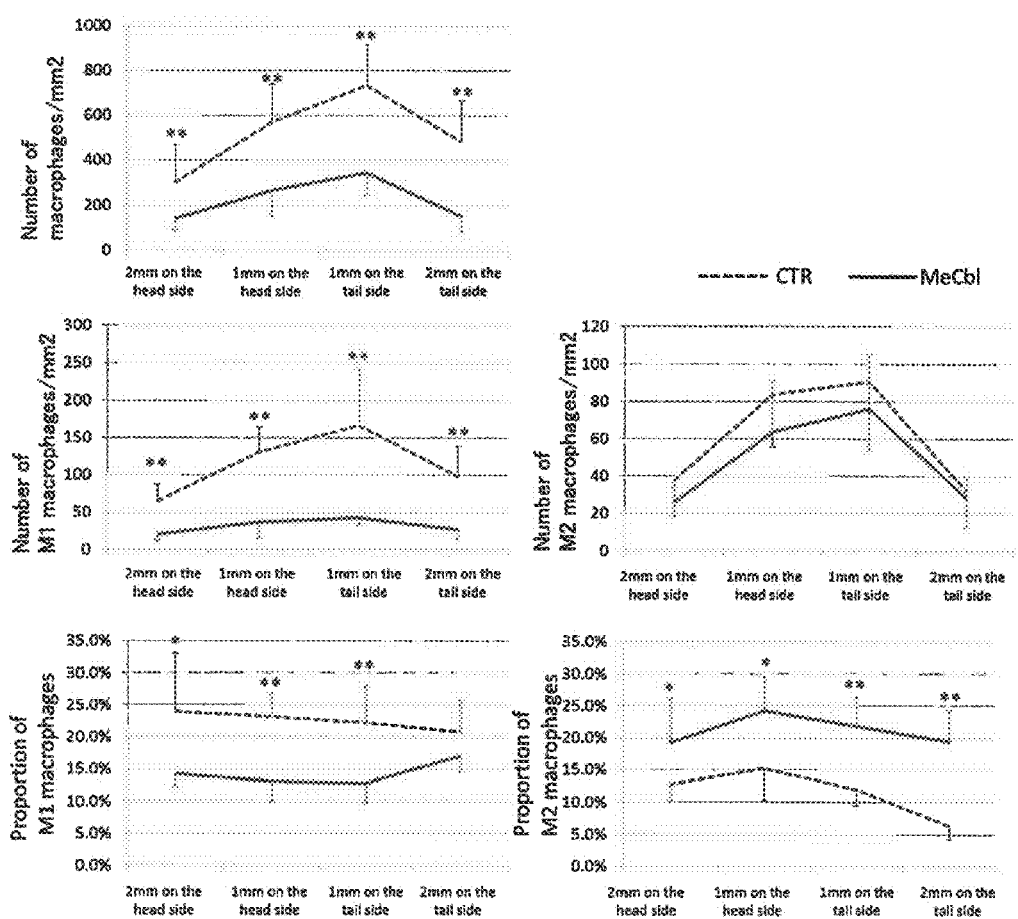

[Fig.17]
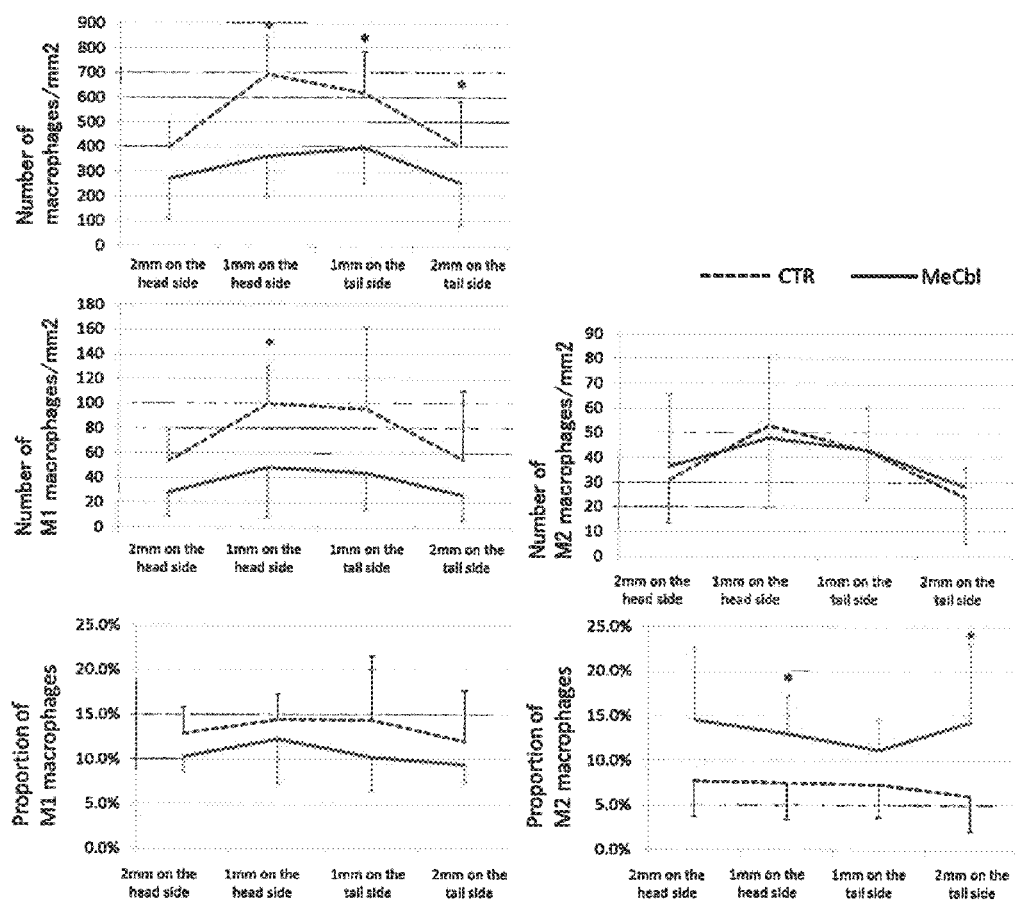

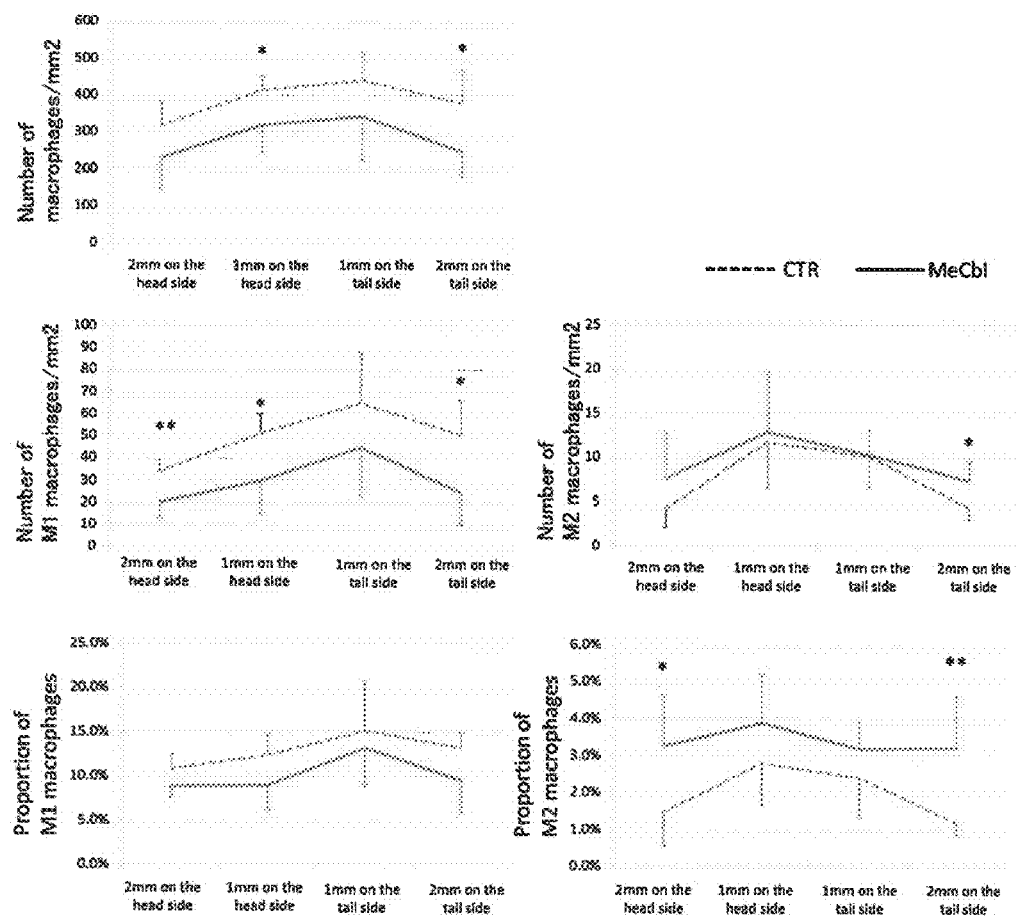
[Fig.18]

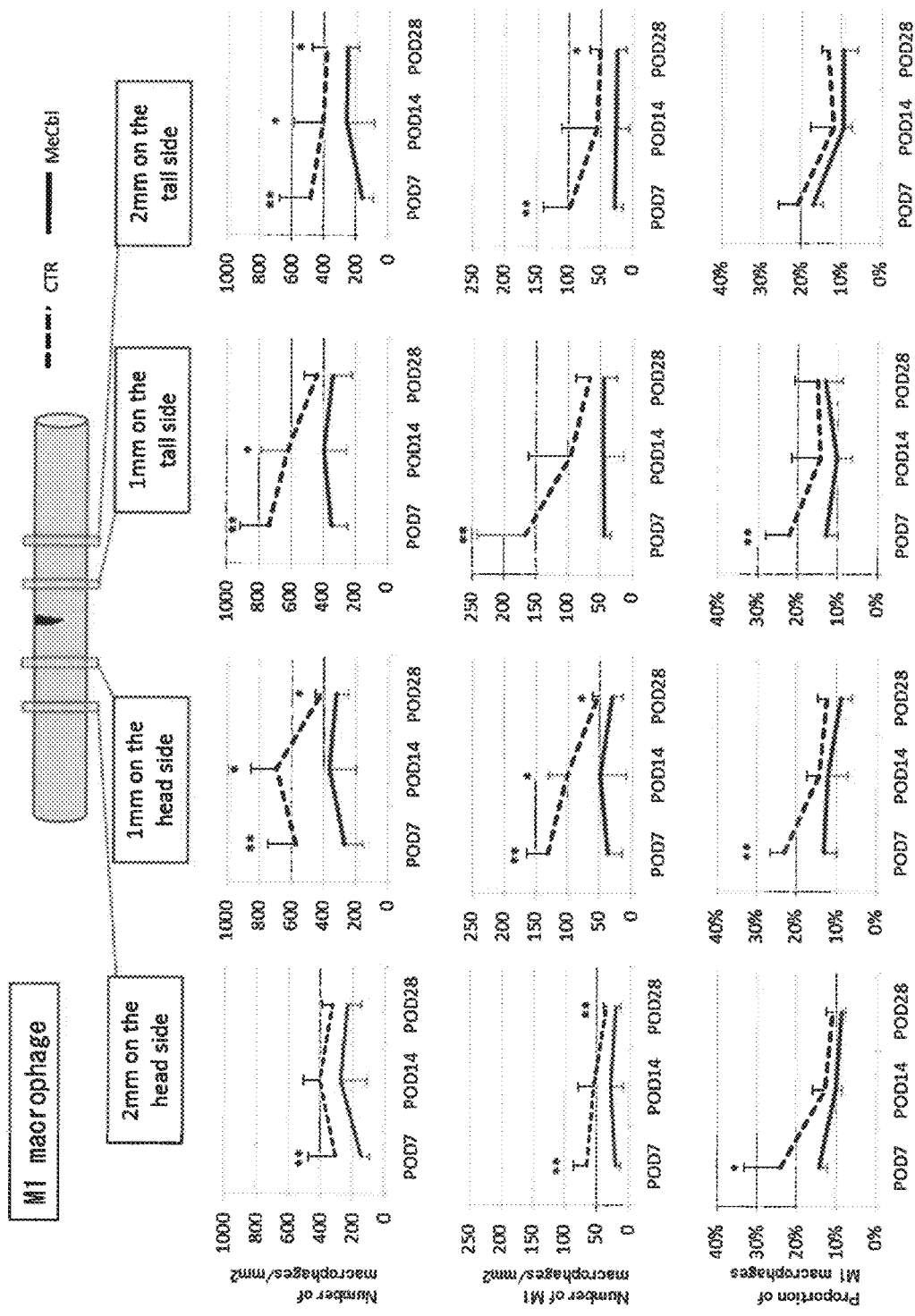
[Fig. 19]

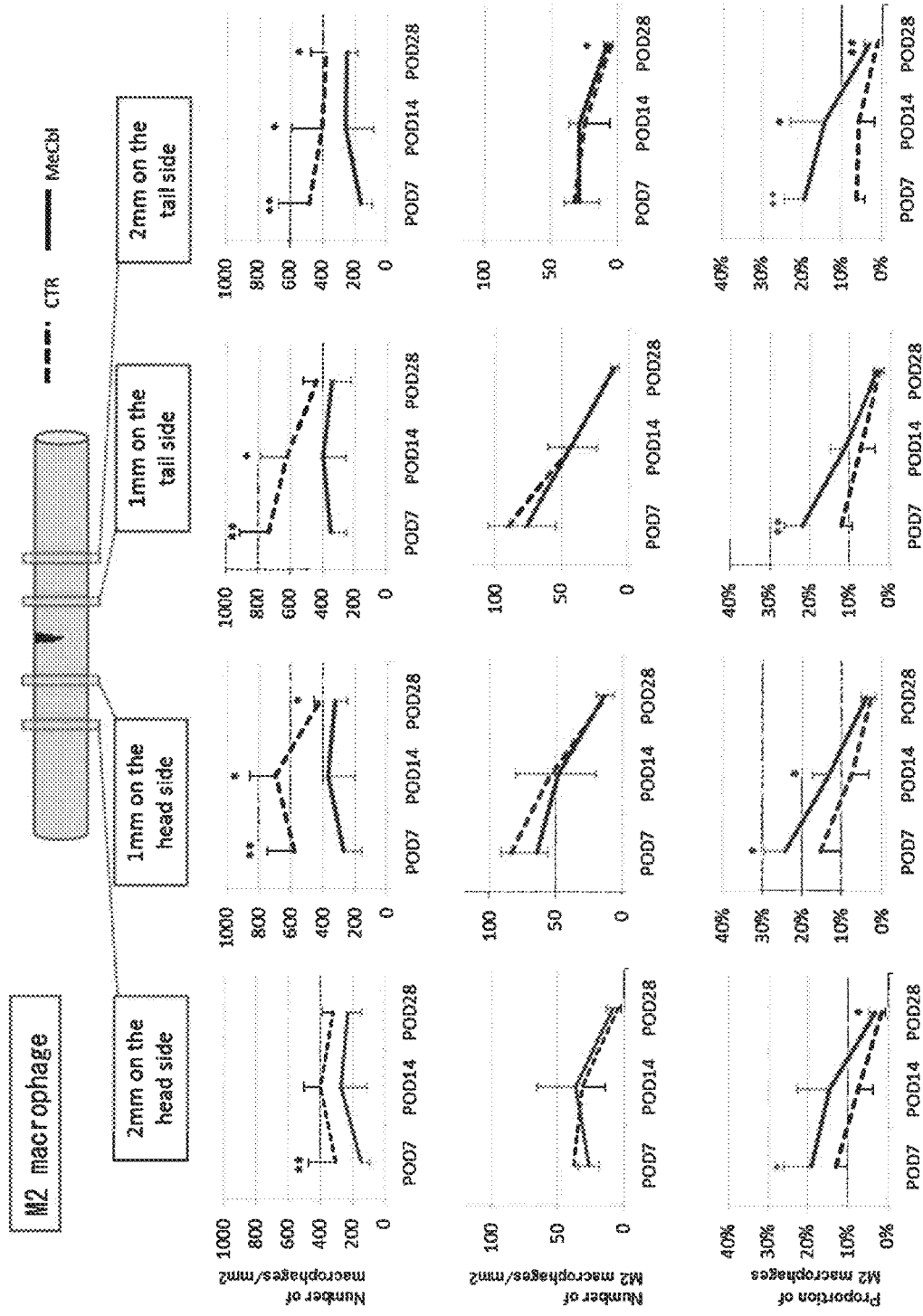
[Fig. 20]

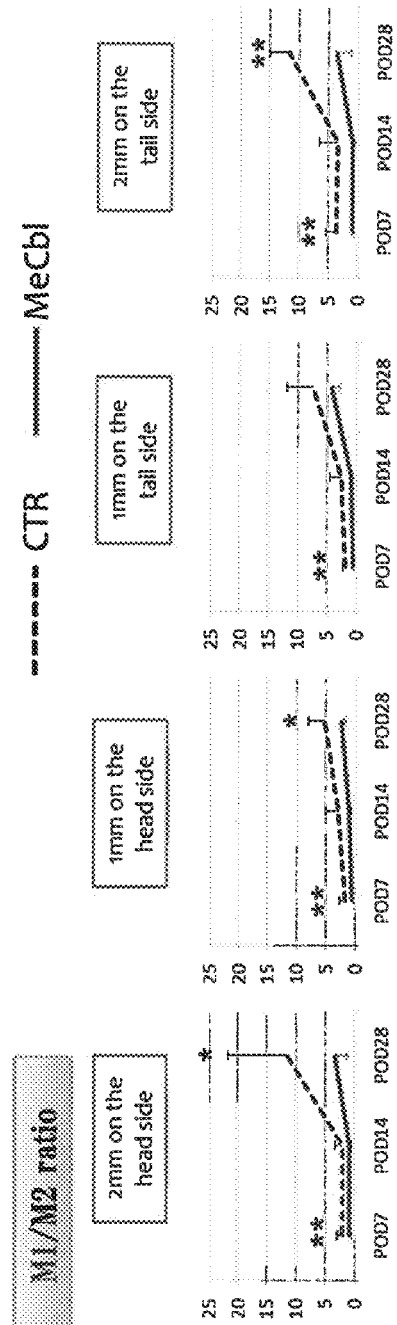
[Fig. 21]

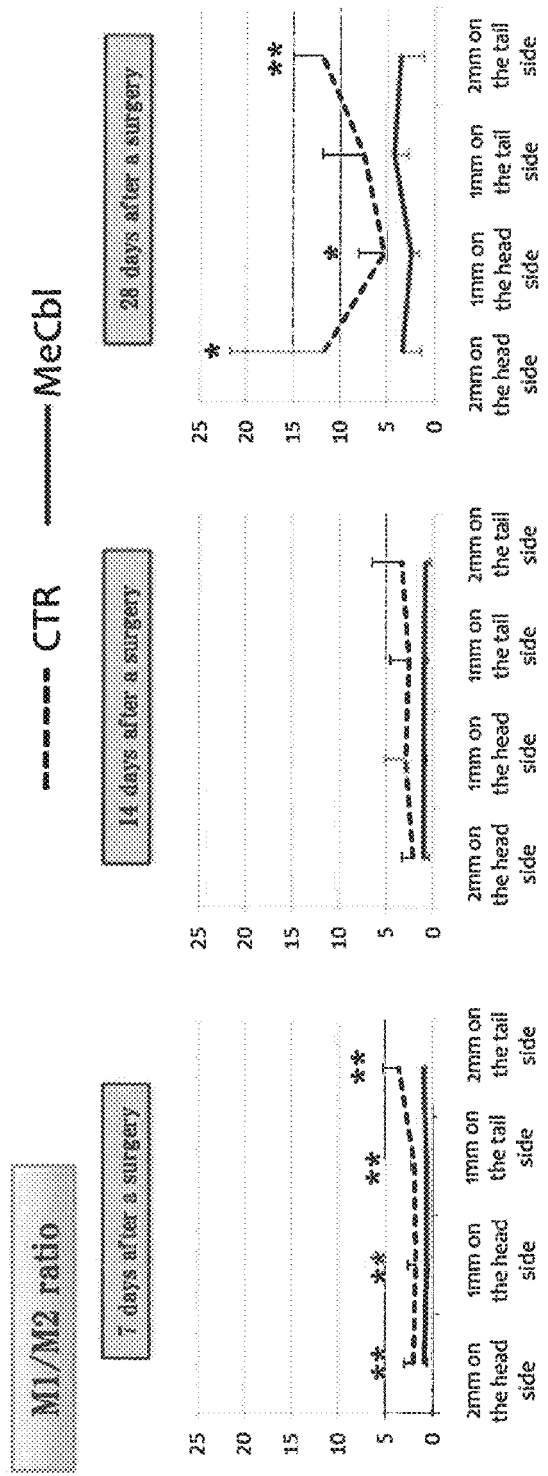
[Fig. 22]

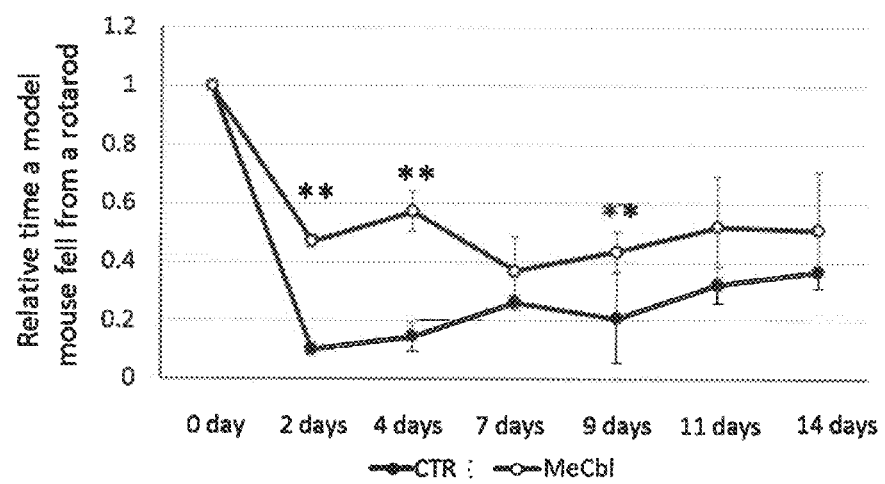
[Fig.23]

THERAPEUTIC AGENT FOR NERVOUS SYSTEM DISEASE

TECHNICAL FIELD

The present invention relates to a therapeutic agent for nervous system disease or the like.

BACKGROUND ART

Nervous system diseases occur in the brain, spinal cord, peripheral nerves, and muscles. Among the diseases, those that affect the brain and spinal cord are referred to as central nervous system diseases. Representative examples of the central nervous system diseases occurring in the brain include cerebral infarction and dementia. Representative examples of the central nervous system diseases occurring in the spinal cord include spinal cord injury.

Cerebral infarction accounted for about 60 percent of cases of cerebrovascular disorder, which was the fourth leading killer for the year of 2014. Given that patients are very likely to need care after having cerebral infarction, the disease greatly affects society in terms of healthcare cost. The zones of cerebral infarction are divided into an ischemic core (also referred to simply as a core), in which blood flow is completely blocked, and a peripheral penumbra (half-shaded zone), in which blood flow is maintained by collateral circulation. While rescuing the core portion, where nerve cells rapidly die (primary injury), is difficult, the penumbral portion may survive because cells escape death in this portion. Thus, how to rescue the penumbral portion is a vital point in acute-phase treatment of cerebral infarction. Histological changes in the cerebral infarction lesion include (1) apoptosis of nerve cells, (2) induction of inflammation, and (3) breakdown of the blood brain barrier (BBB). Examples of cerebral infarction therapeutic agents currently used in Japan include urokinase, anticoagulation agents, and antiplatelet agents, as well as agents that dilute blood and agents that reduce edema. Edaravone (trade name, Radicut) was approved as a drug for scavenging free radicals in Japan in 2001 but has not been approved in Europe, the United States, or the like. A thrombolytic therapy (tissue plasminogen activator [tPA] therapy) was approved in 2005, but its use is restricted to treatment given within 4.5 hours from the onset of the disease. Then, no additional therapeutic drug for cerebral infarction has become available since 2005.

It is reported that there are about 5000 new patients with spinal cord injury each year in Japan. Pain, numbness, motor dysfunction, and the like are associated with an extremely decreased QOL of patients. Pathogenesis of spinal cord injury involves damage to nerve cells and vascular tissue due to a direct external force at the time of injury (primary injury), followed by a series of reactions associated with the breakdown of the blood-spinal cord barrier (secondary injury), which results in expansion of the injured area. Since the primary injury is inevitable, how to reduce the secondary injury is critical in the acute to subacute-phase treatment of spinal cord injury. However, no safe and effective therapeutic drug is currently available for the treatment of acute-phase spinal cord injury in clinical setting. The treatment guidelines for acute spinal cord injury issued in the United States clearly state that conventional therapies using high-dose methylprednisolone should not be used routinely because of their severe side effects. Thus, there is an unmet medical need for a novel therapeutic agent effective for spinal cord injury.

Peripheral nerves have a capacity to regenerate after injury, but it is not sufficient for restoring neural functions. When a nerve is injured, Wallerian degeneration, i.e., phagocytotic elimination of axons and myelin sheaths, occurs. In the subsequent regeneration process, a regenerated axon extends in a distal direction along the Bungner's band formed by undifferentiated Schwann cells, leading to reinnervation of the target muscle. Eventually, a myelin sheath is formed by Schwann cells which surround the regenerated axon. However, the regenerated nerve extends at a very low rate, and muscular atrophy occurs if the distance to the target muscle is long; thus, sufficient functional recovery cannot be expected. In recent years, it has been found that macrophages play an important role in each step of the regeneration process, and this finding is attracting attention. While the pro-inflammatory function of macrophages is well known, there is also another phenotype that has an anti-inflammatory function, opposite to it, and these two phenotypes, referred to as an M1 and an M2, respectively, are viewed as a continuum (switch between M1 and M2 can occur). In general, it is said that nerve regeneration can be promoted by increasing M2 macrophage, which is an anti-inflammatory phenotype.

On the other hand, central nervous system is known to have a lower capacity to regenerate compared with peripheral nervous system. It is known that, after central nerve injury, an axon outgrowth inhibitor is expressed in oligodendrocytes, which are cells forming a myelin sheath around an axon, and that macrophage/microglia, astrocyte, and the like form glial scar, which exerts an inhibitory effect on axon outgrowth. It is therefore said that suppression of the pro-inflammatory effect of macrophage/microglia is important after central nerve injury, and that nerve regeneration can be promoted by increasing M2 macrophage/microglia, which is an anti-inflammatory phenotype, as with peripheral nervous system.

It is known that vitamin $B_{12}$ is effective for treating vitamin $B_{12}$ deficiency, and that neurologic changes, such as peripheral neuritis or spinal cord change, may occur in vitamin $B_{12}$ deficiency (Patent Document 1).

In addition, patients with cerebral ischemia have an elevated blood level of homocysteine as compared with healthy individuals, suggesting an association between the blood homocysteine level and cerebral ischemia. Further, it has been found that the blood homocysteine level is decreased by administration of folic acid, vitamin $B_6$, and vitamin $B_{12}$, suggesting that decreases in the homocysteine level can potentially reduce the risk of cerebral ischemia (Non-Patent Document 1).

Moreover, it is known that activins exert an anti-inflammatory effect by inducing M2 macrophage (Patent Document 2), and that an immunosuppressive agent containing adipose tissue-derived mesenchymal stem cells induces M2 macrophage (Patent Document 3).

However, it has not been disclosed that vitamin $B_{12}$ promotes M2 macrophage/microglia induction, inhibits M1 macrophage/microglia induction, and alleviates neurological diseases such as cerebral infarction.

PRIOR ART DOCUMENTS

Patent Documents

Patent Document 1: Japanese Patent Laid-Open No. 2016-513694
Patent Document 2: International Publication No. WO 2011/149036
Patent Document 3: International Publication No. WO 2011/043136

Non-Patent Document

Non-Patent Document 1: Current Medicinal Chemistry, 2007, Vol. 14, No. 3, p. 249-263

SUMMARY OF THE INVENTION

Problem to be Solved by the Invention

An object of the present invention is to provide a therapeutic agent for nervous system disease. Preferably, an object of the present invention is to provide a therapeutic agent for nervous system disease having at least one selected from the group consisting of an apoptosis inhibiting effect, a necrosis inhibiting effect, an axon outgrowth promoting effect, an M2 macrophage/microglia induction promoting effect, an M1 macrophage/microglia induction inhibiting effect, and a nerve regeneration promoting effect.

Means for Solving the Problems

The present inventors have made extensive investigations in view of the above problems and have found that vitamin $B_{12}$ has a therapeutic effect on nervous system diseases. In addition, the present inventors also have found that vitamin $B_{12}$ has an apoptosis inhibiting effect, a necrosis inhibiting effect, an axon outgrowth promoting effect, an M2 macrophage/microglia induction promoting effect, an M1 macrophage/microglia induction inhibiting effect, a nerve regeneration promoting effect, and the like. The present inventors have made further investigations based on these findings and have accomplished the present invention.

Specifically, the present invention encompasses the following aspects:

Item 1. A therapeutic agent for nervous system disease comprising vitamin $B_{12}$.

Item 1A. A method of treating a nervous system disease, the method comprising administering vitamin $B_{12}$ to a patient in need of treatment of a nervous system disease.

Item 1B1. Vitamin $B_{12}$ for use in treating a nervous system disease.

Item 1B2. A composition comprising vitamin $B_{12}$ for use in treating a nervous system disease.

Item 1C. Use of vitamin $B_{12}$ for the manufacture of a therapeutic agent for nervous system disease.

Item 2. The therapeutic agent for nervous system disease according to Item 1, wherein the therapeutic agent for nervous system disease is an M2 macrophage/microglia induction promoting agent.

Item 3. The therapeutic agent for nervous system disease according to Item 1, wherein the therapeutic agent for nervous system disease is an M1 macrophage/microglia induction inhibiting agent.

Item 4. The therapeutic agent for nervous system disease according to any one of Items 1 to 3, wherein the therapeutic agent for nervous system disease is a nerve regeneration promoting agent.

Item 5. The therapeutic agent for nervous system disease according to any one of Items 1 to 4, wherein the nervous system disease is a central nervous system disease.

Item 6. The therapeutic agent for nervous system disease according to Item 5, wherein the central nervous system disease is a cerebrovascular disease.

Item 7. The therapeutic agent for nervous system disease according to Item 6, wherein the cerebrovascular disease is at least one selected from the group consisting of cerebral infarction, cerebral hemorrhage, cerebral thrombosis, cerebral arteriosclerosis, and dementia.

Item 8. The therapeutic agent for nervous system disease according to any one of Items 1 to 4, wherein the nervous system disease is nerve injury.

Item 9. The therapeutic agent for nervous system disease according to Item 8, wherein the nerve injury is central nerve injury.

Item 10. The therapeutic agent for nervous system disease according to Item 9, wherein the central nerve injury is spinal cord injury.

Item 11. The therapeutic agent for nervous system disease according to any one of Items 1 to 10, wherein the vitamin $B_{12}$ is at least one selected from the group consisting of methylcobalamin, cyanocobalamin, hydroxocobalamin, sulfitocobalamin, adenosylcobalamin, and salts thereof.

Item 12. The therapeutic agent for nervous system disease according to any one of Items 1 to 11, wherein the vitamin $B_{12}$ is methylcobalamin.

Item 13. The therapeutic agent for nervous system disease according to any one of Items 1 to 12, wherein the therapeutic agent for nervous system disease is used for continuous administration.

Item 14. The therapeutic agent for nervous system disease according to Item 13, wherein the therapeutic agent for nervous system disease is a formulation for intravenous drip infusion.

Item 15. The therapeutic agent for nervous system disease according to any one of Items 1 to 14, wherein the therapeutic agent for nervous system disease is used so that administration is started at 12 to 24 hours after onset of the disease.

Item 16. The therapeutic agent for nervous system disease according to any one of Items 1 to 14, wherein the therapeutic agent for nervous system disease is used so that administration is started immediately after onset of the disease or within 12 hours of the onset.

BRIEF DESCRIPTION OF DRAWINGS

FIG. 1 shows the results of TUNEL assay in Example 1. The vertical axis indicates the proportion of apoptotic cells. The horizontal axis indicates types of drugs added and whether the drugs were added (+) or not (−). Two asterisks "**" indicates that the result of a statistical analysis using the Tukey-Kramer method had a p value of less than 0.01.

FIG. 2 shows the results of lactate dehydrogenase (LDH) assay in Example 2. The vertical axis indicates LDH activity, which is an index of necrosis, as a percentage with respect to that in a high control. The horizontal axis indicates a type of a drug added and whether the drug was added (10 µM) or not (−). An asterisk "*" indicates that the result of a statistical analysis using Student's t-test had a p value of less than 0.05.

FIG. 3 shows the results of a neurite outgrowth assay in Example 3. The vertical axis indicates the average length of 30 or more neural axons. The horizontal axis indicates concentrations of a drug added. The control (CTR) contains no drug. An asterisk "*" indicates that the result of a statistical analysis using Dunnett's test against CTR had a p value of less than 0.05, and "**" indicates that the result had a p value of less than 0.01.

FIG. 4 shows the results of 2,3,5-triphenyltetrazolium chloride (TTC) staining in Example 4. The vertical axis indicates the ischemic lesion volume. The horizontal axis indicates a type of a drug added and whether the drug was added (MeCbl) or not (Control). Two asterisks "**" indicates that the result of a statistical analysis using Student's t-test had a p value of less than 0.01.

FIG. 5 shows the results of Western blot in Example 5. The vertical axes indicate the ratio of the amount of an M1 marker (left graph, IL-1β protein; right graph, iNOS protein) to the amount of glyceraldehyde-3-phosphate dehydrogenase (GAPDH) protein. The horizontal axes indicate types of drugs added and whether the drugs were added (+ or concentration) or not (−). An asterisk "*" indicates that the result of a statistical analysis using Dunnett's test had a p value of less than 0.05, and "**" indicates that the result had a p value of less than 0.01.

FIG. 6 shows the results of Western blot in Example 5. The vertical axes indicate the ratio of the amount of an M2 marker (left graph, arginase I (Arg1) protein; right graph, CD206 protein) to the amount of GAPDH protein. The horizontal axes indicate types of drugs added and whether the drugs were added (+ or concentration) or not (−). An asterisk "*" indicates that the result of a statistical analysis using Dunnett's test had a p value of less than 0.05, and "**" indicates that the result had a p value of less than 0.01.

FIG. 7 shows the results of an immunohistological evaluation in Example 5. The vertical axes indicate the percentage of M1 macrophages (percentage of iNOS-positive cells) in the left graph and the percentage of M2 macrophages (percentage of Arg1-positive cells) in the right graph. The horizontal axes indicate types of drugs added and whether the drugs were added (+ or concentration) or not (−). Two asterisks "**" indicates that the result of a statistical analysis using Dunnett's test had a p value of less than 0.01.

FIG. 8-1 shows the results of Western blot in Example 6. The vertical axis indicates the ratio of the amount of phosphorylated Akt protein to the amount of Akt protein. The horizontal axes indicate types of drugs added and whether the drugs were added (+ or concentration) or not (−). An asterisk "*" indicates that the result of a statistical analysis using the Tukey-Kramer method had a p value of less than 0.05, "" indicates that the result had a p value of less than 0.01, and "*" indicates that the result had a p value of less than 0.001.

FIG. 8-2 shows the results of Western blot in Example 6. The vertical axis indicates the ratio of the amount of phosphorylated 4EBP1 protein to the amount of 4EBP1 protein. The horizontal axes indicate types of drugs added and whether the drugs were added (+or concentration) or not (−). An asterisk "*" indicates that the result of a statistical analysis using the Tukey-Kramer method had a p value of less than 0.05, "" indicates that the result had a p value of less than 0.01, and "*" indicates that the result had a p value of less than 0.001.

FIG. 8-3 shows the results of Western blot in Example 6. The vertical axis indicates the ratio of the amount of phosphorylated S6K protein to the amount of S6K protein. The horizontal axes indicate types of drugs added and whether the drugs were added (+or concentration) or not (−). An asterisk "*" indicates that the result of a statistical analysis using the Tukey-Kramer method had a p value of less than 0.05, "" indicates that the result had a p value of less than 0.01, and "*" indicates that the result had a p value of less than 0.001.

FIG. 9 shows the results of immunohistological evaluation in Example 7. Graphs, from the left row, show the results at 2.5 mm in the proximal direction from an injury site, the injury site, and 2.5, 5.0, and 7.5 mm in the distal direction. The vertical axes indicate the number of macrophages in the upper graphs, the number of M1 macrophages in the middle graphs, and the proportion of M1 macrophages in the lower graphs. The horizontal axes indicate the number of days elapsed after occurrence of sciatic nerve injury. CTR refers to an untreated group, MeCbl refers to a methylcobalamin treatment group, and Sham refers to a non-injury group, which underwent only sciatic nerve exteriorization. An asterisk "*" indicates that the result of a statistical analysis using the Tukey-Kramer method (CTR vs. MeCbl) had a p value of less than 0.05, and "#" indicates that the result of a statistical analysis using Student's t-test (CTR vs. MeCbl) had a p value of less than 0.05.

FIG. 10 shows the results of immunohistological evaluation in Example 7. Graphs, from the left row, show the results at 2.5 mm in the proximal direction from an injury site, the injury site, and 2.5, 5.0, and 7.5 mm in the distal direction. The vertical axes indicate the number of macrophages in the upper graphs, the number of M2 macrophages in the middle graphs, and the proportion of M2 macrophages in the lower graphs. The horizontal axes indicate the number of days elapsed after occurrence of sciatic nerve injury. CTR refers to an untreated group, MeCbl refers to a methylcobalamin treatment group, and Sham refers to a non-injury group, which underwent only sciatic nerve exteriorization. An asterisk "*" indicates that the result of a statistical analysis using the Tukey-Kramer method (CTR vs. MeCbl) had a p value of less than 0.05, and "#" indicates that the result of a statistical analysis using Student's t-test (CTR vs. MeCbl) had a p value of less than 0.05.

FIG. 11 shows the results of an immunohistological evaluation in Example 8. The vertical axes indicate the number of axons in the upper graph, the number of myelinated axons in the middle graph, and the myelination ratio in the lower graph. The horizontal axes represent positions at which transverse sections of a nerve were prepared (from left, 2.5 mm in the proximal direction from an injury site, the injury site, and 2.5, 5.0, and 7.5 mm in the distal direction). CTR refers to an untreated group, MeCbl refers to a methylcobalamin treatment group, and Sham refers to a non-injury group, which underwent only sciatic nerve exteriorization. An asterisk "*" indicates that the result of a statistical analysis using the Tukey-Kramer method (CTR vs. MeCbl) had a p value of less than 0.05.

FIG. 12 shows the results of measurement of BBB scores in Example 9. The vertical axis indicates the BBB score. The horizontal axis indicates the number of days elapsed after a surgery for constructing a spinal cord injury model, with 0 indicating pre-surgery. CTR refers to an untreated group, MeCbl refers to a methylcobalamin treatment group, and Sham refers to a non-injury group, which underwent only sciatic nerve exteriorization. An asterisk "*" indicates that the result of a statistical analysis using Steel-Dwass test (CTR vs. MeCbl) had a p value of less than 0.05.

FIG. 13 shows the results of thermal algesimetry test in Example 9. The vertical axis indicates the time after applying infrared thermal stimulation to the right sole of the hind limb of a model rat until the rat retracted the limb because of the applied heat. The horizontal axis indicates the number of days elapsed after a surgery for constructing a spinal cord injury model, with 0 indicating pre-surgery. CTR refers to an untreated group, MeCbl refers to a methylcobalamin treatment group, and Sham refers to a non-injury group, which underwent only sciatic nerve exteriorization. An asterisk "*" indicates that the result of a statistical analysis using Steel-Dwass test (CTR vs. MeCbl) had a p value of less than 0.05.

FIG. 14 shows the results of Western blot of M1 markers (IL-1β protein and iNOS protein) in Example 10. The vertical axes indicate the ratio of the amount of the M1 marker (IL-1β protein or iNOS protein) to the amount of GAPDH protein. The horizontal axes indicate types of drugs added and whether the drugs were added (+ or concentration) or not (−). An asterisk "*" indicates that the result of a statistical analysis using Dunnett's test had a p value of less than 0.05, and "**" indicates that the result had a p value of less than 0.01.

FIG. 15 shows the results of Western blot of M2 markers (Arg1 protein and CD206 protein) in Example 10. The vertical axes, the horizontal axes, and each symbol have the same meaning as described for FIG. 14.

FIG. 16 shows the results of immunofluorescent staining at 7 days after the surgery in Example 11. Each graph shows difference depending on the position. The horizontal axis in each graph indicates the direction and distance from an injury site. The vertical axes indicate the number of macrophages in the upper graphs, the number of M1 or M2 macrophages in the middle graphs, and the proportion of M1 or M2 macrophages in the lower graph. CTR refers to an untreated group, and MeCbl refers to a methylcobalamin treatment group. An asterisk "*" indicates that the result of a statistical analysis using Mann Whitney U test (CTR vs. MeCbl) had a p value of less than 0.05, and "**" indicates that the result had a p value of less than 0.01.

FIG. 17 shows the results of immunofluorescent staining at 14 days after the surgery in Example 11 and is otherwise the same as FIG. 16.

FIG. 18 shows the results of immunofluorescent staining at 28 days after the surgery in Example 11 and is otherwise the same as FIG. 16.

FIG. 19 shows the results of immunofluorescent staining of M1 macrophage in Example 11. Each graph shows difference depending on the number of days elapsed after the surgery. Graphs in each row show the results according to the direction and distance from an injury site: 2 and 1 mm on the head side and 1 and 2 mm on the tail side. The vertical axes indicate the number of macrophages in the upper graphs, the number of M1 macrophages in the middle graphs, and the proportion of M1 macrophages in the lower graph. The horizontal axes indicate the number of days elapsed after the surgery for constructing a spinal cord injury model. CTR refers to an untreated group, and MeCbl refers to a methylcobalamin treatment group. An asterisk "*" indicates that the result of a statistical analysis using Mann Whitney U test (CTR vs. MeCbl) had a p value of less than 0.05, and "**" indicates that the result had a p value of less than 0.01.

FIG. 20 shows the results of immunofluorescent staining of M2 macrophage in Example 11 and is otherwise the same as FIG. 19.

FIG. 21 shows the results of immunofluorescent staining for the M1/M2 ratio in Example 11. Each graph shows difference depending on the number of days elapsed after the surgery. The graphs show the results according to the direction and distance from the injury site: 2 and 1 mm on the head side and 1 and 2 mm on the tail side. The vertical axes indicate the M1/M2 ratio. The horizontal axes indicate the number of days elapsed after the surgery for constructing a spinal cord injury model. CTR refers to an untreated group, and MeCbl refers to a methylcobalamin treatment group. An asterisk "*" indicates that the result of a statistical analysis using Mann Whitney U test (CTR vs. MeCbl) had a p value of less than 0.05, and "**" indicates that the result had a p value of less than 0.01.

FIG. 22 shows the results of immunofluorescent staining for the M1/M2 ratio in Example 11. Each graph shows difference depending on the position. The graphs, from left, show the results at 7, 14, and 28 days after a surgery for constructing a spinal cord injury model. The vertical axes indicate the M1/M2 ratio. The horizontal axes indicate the number of days elapsed after the surgery for constructing a spinal cord injury model. The horizontal axes indicate the direction and distance from the injury site. CTR refers to an untreated group, and MeCbl refers to a methylcobalamin treatment group. An asterisk "*" indicates that the result of a statistical analysis using Mann Whitney U test (CTR vs. MeCbl) had a p value of less than 0.05, and "**" indicates that the result had a p value of less than 0.01.

FIG. 23 shows the results of a rotarod test in Example 12. The horizontal axis indicates the number of days elapsed after a surgery creating cerebral infarction, and the vertical axis indicates relative time until a model mouse fell from a rotarod. CTR refers to an untreated group, and MeCbl refers to a methylcobalamin treatment group. Two asterisks "**" indicates that the result of a statistical analysis using Mann Whitney U test (CTR vs. MeCbl) had a p value of less than 0.01.

Mode for Carrying Out the Invention

As used herein, the expressions "containing" and "comprising" encompass concepts of "containing," "comprising," "substantially comprising," and "consisting of."

As used herein, the term "macrophage/microglia" refers to "macrophages and/or microglia" and encompasses both the meaning of "macrophages and microglia" and the meaning of "macrophages or microglia."

In one aspect, the present invention relates to a therapeutic agent for nervous system disease, an apoptosis inhibiting agent, a necrosis inhibiting agent, an axon outgrowth promoting agent, an M2 macrophage/microglia induction promoting agent, an M1 macrophage/microglia induction inhibiting agent, a nerve regeneration promoting agent, or the like that contains vitamin $B_{12}$ (herein, may also be referred to as an "agent of the present invention"). These agents will be described below.

1. Active Ingredient

Vitamin $B_{12}$ includes cobalamin, derivatives thereof, and salts of the foregoing. Specific examples of vitamin $B_{12}$ include cobalamin, a cobalt substitution product of cobalamin, and derivatives thereof. More specific examples include methylcobalamin, cyanocobalamin, hydroxocobalamin, sulfitocobalamin, adenosylcobalamin, and salts thereof. Among these, methylcobalamin, cyanocobalamin, hydroxocobalamin, and salts thereof are preferred, and methylcobalamin and salts thereof are more preferred.

The salts of cobalamin and derivatives thereof are not particularly limited as long as the salts are pharmacologically acceptable, and both acid salts and basic salts can be used. Examples of the acid salt include inorganic acid salts such as hydrochlorides, hydrobromides, sulfates, nitrates, and phosphates; organic acid salts such as acetates, propionates, tartrates, fumarates, maleates, malates, citrates, methanesulfonates, and p-toluenesulfonates; and amino acid salts such as aspartates and glutamates. Examples of the basic salt include alkali metal salts such as sodium salts and potassium salts; and alkaline-earth metal salts such as calcium salts and magnesium salts.

Vitamin $B_{12}$ may be in the form of solvates. The solvents are not particularly limited as long as the solvents are pharmacologically acceptable, and examples include water, ethanol, glycerol, and acetic acid.

As Vitamin $B_{12}$, one type may be used alone, or two or more type may be used in combination.

2. Use

Vitamin $B_{12}$ has a therapeutic effect on a nervous system disease. Therefore, vitamin $B_{12}$ can be used as an active ingredient in a therapeutic agent for nervous system disease.

Vitamin $B_{12}$ has an apoptosis inhibiting effect, a necrosis inhibiting effect, an axon outgrowth promoting effect, an M2 macrophage/microglia induction promoting effect, an M1 macrophage/microglia induction inhibiting effect, a nerve regeneration promoting effect, and the like. Therefore, vitamin $B_{12}$ can be used as an active ingredient of agents such as an apoptosis inhibiting agent, a necrosis inhibiting agent, an axon outgrowth promoting agent, an M2 macrophage/microglia induction promoting agent, an M1 macrophage/microglia induction inhibiting agent, an M1:M2 ratio (ratio of M1 macrophage/microglia to M2 macrophage/microglia) reducing agent, or a nerve regeneration promoting agent.

In addition, vitamin $B_{12}$ may be used as an active ingredient in a preferred form of the therapeutic agent for nervous system disease, which is an active ingredient in a therapeutic agent for nervous system disease based on at least one selected from the group consisting of an apoptosis inhibiting effect, a necrosis inhibiting effect, an axon outgrowth promoting effect, an M2 macrophage/microglia induction promoting effect, an M1 macrophage/microglia induction inhibiting effect, and a nerve regeneration promoting effect.

The nervous system disease is not particularly limited and includes a central nervous system disease and a peripheral nervous system disease. Examples of the central nervous system disease include a cerebrovascular disease and central nervous system injury.

Examples of the cerebrovascular disease include cerebral infarction, cerebral hemorrhage, cerebral thrombosis, cerebral arteriosclerosis, and dementia.

The nerve injury may be either peripheral nerve injury or central nerve injury. The central nerve injury includes spinal cord injury. Causes of the nerve injury are not particularly limited, and nerve injuries of a variety of causes, such as traumatic injury, pressure caused by a plaster cast, electrical injury, disk herniation, or radiation exposure may be applicable. The severity of applicable nerve injuries is not particularly limited, and applicable cases include all of cases including a case where axons are preserved but demyelination has occurred, a case where Wallerian degeneration is accompanied, and a case where nerves are anatomically divided. The nerve injury encompasses various symptoms associated with the nerve injury including, for example, dyskinesia (e.g., motor paralysis and muscle weakness in upper and lower extremities), sensory disorder (e.g., hypesthesia, numbness, and pain), autonomic nerve disorder (e.g., dyshidrosis, change of skin color), or the like in an injured innervation area.

The nervous system disease is preferably a nervous system disease that can be treated by at least one selected from the group consisting of an apoptosis inhibiting effect, a necrosis inhibiting effect, an axon outgrowth promoting effect, an M2 macrophage/microglia induction promoting effect, an M1 macrophage/microglia induction inhibiting effect, and a nerve regeneration promoting effect.

An agent of the present invention is not particularly limited as long as the agent contains vitamin $B_{12}$ (as used herein, may be referred to simply as an "active ingredient") and may contain other ingredients, if necessary. The other ingredients are not limited as long as the ingredients are pharmacologically acceptable. The other ingredients include additives in addition to an ingredient having a pharmacological action. Examples of the additives include bases, carriers, solvents, dispersants, emulsifiers, buffers, stabilizers, excipients, binders, disintegrants, lubricants, thickeners, humectants, colorants, flavoring agents, and chelating agents.

Vitamin $B_{12}$ used alone can exert a nervous system disease therapeutic effect, an apoptosis inhibiting effect, a necrosis inhibiting effect, an axon outgrowth promoting effect, an M2 macrophage/microglia induction promoting effect, an M1 macrophage/microglia induction inhibiting effect (here, an effect of switching M1 macrophage/microglia to M2 macrophage/microglia is not ruled out), a nerve regeneration promoting effect, and the like. Therefore, the agent of the present invention can exert the desired effect without containing other ingredients having these effects and/or actions. However, the agent of the present invention can contain other ingredients having a pharmacological action.

Modes of use for the agent of the present invention are not particularly limited, and a suitable mode of use can be selected according to the type of the agent. The agent of the present invention can be used in vitro (e.g., added to a medium of cultured cells) or in vivo (e.g., administered to animals), for example, depending on the purpose.

Targets for application of the agent of the present invention are not particularly limited. Examples of target mammals include humans, monkeys, mice, rats, dogs, cats, rabbits, pigs, horses, cattle, sheep, goats, and deer. Examples of target cells include animal cells. Types of cells are not particularly limited either, and examples include blood cells, hematopoietic stem cells, progenitor cells, gametes (sperm and ovum), fibroblasts, epithelial cells, vascular endothelial cells, nerve cells, hepatic cells, keratinocytes, muscle cells, epidermal cells, endocrine cells, ES cells, iPS cells, tissue stem cells, and cancer cells.

The agent of the present invention can be in any dosage form. Examples of the dosage form include oral dosage forms such as tablets (including orally disintegrating tablets, chewable tablets, foam tablets, lozenges, and gelatinous drop formulations), pills, granules, fine granules, powders, hard capsules, soft capsules, dry syrup preparations, liquids (including drinkable formulations, suspensions, and syrups), and jelly formulations; and parenteral dosage forms such as injection formulations (e.g., drip infusions [e.g., formulations for intravenous drip infusion], intravenous injections, intramuscular injections, subcutaneous injections, and intradermal injections), topical agents (e.g., ointments, plasters, and lotions), suppositories, inhalants, ophthalmic formulations, ophthalmic ointments, nasal drops, ear drops, and liposome formulations.

Administration routes of the agent of the present invention are not particularly limited as long as a desired effect can be achieved, and examples include oral administration and parenteral administration including enteral administration, such as tube feeding and enema administration, intravenous administration, intraarterial administration, intramuscular administration, intracardiac administration, subcutaneous administration, intradermal administration, and intraperitoneal administration.

The content of an active ingredient in the agent of the present invention is not limited and varies depending on the mode of use, the application target, conditions of the application target, and the like. For example, the content can be 0.0001 to 100 wt % and preferably 0.001 to 50 wt %.

The dose of the agent of the present invention for administration to animals is not particularly limited as long as the dose is an effective dose, which produces medicinal benefit. The usual dose (weight of an active ingredient) is 0.1 to 1000 mg/kg body weight per day and preferably 0.5 to 500 mg/kg body weight per day for oral administration; and 0.01 to 100 mg/kg body weight per day and preferably 0.05 to 50 mg/kg body weight per day for parenteral administration. The above-described doses may be suitably adjusted depending on the age, pathological conditions, and symptoms.

The agent of the present invention is preferably used by continuous administration from the viewpoint of further effectively achieving the M2 macrophage/microglia induction promoting effect, the M1 macrophage/microglia induction inhibiting effect, the nerve regeneration promoting effect, or the like. By continuous administration, the concentration of an active ingredient, which acts on cells in the target of administration (e.g., cells in the affected area of a nervous system disease, preferably macrophage/microglia), can be maintained within concentrations suitable for achieving the M2 macrophage/microglia induction promoting effect, the M1 macrophage/microglia induction inhibiting effect, and the nerve regeneration promoting effect (e.g., 5 to 100 μM, preferably 10 to 50 μM, more preferably 20 to 10 μM, still more preferably 50 to 5 μM, and even more preferably 100 to 1 μM), and the effects can be more effectively achieved. In addition, the agent of the present invention is preferably a drip infusion, and more preferably a formulation for intravenous drip infusion, although depending on the target of application.

Timing for administration of the agent of the present invention is not particularly limited.

As an example, the agent of the present invention is used so that administration of the agent is started at 12 to 24 hours after onset of the disease. The onset is a time when a symptom of a disease or a factor directly causing the disease can be recognized. For example, the onset is a time at which an ischemic lesion develops in an ischemic cerebrovascular disease such as cerebral infarction. Since the agent of the present invention can act on the repair mechanism, which can operate relatively long after the development of the ischemic lesion (an M2 macrophage/microglia induction promoting effect, an M1 macrophage/microglia induction inhibiting effect, and a nerve regeneration promoting effect), therapeutic effects can be achieved even if the agent is administered at the above-described timing (at 12 to 24 hours after onset) in the application of the agent to an ischemic cerebrovascular disease such as cerebral infarction.

As another example, the agent of the present invention is used so that administration of the agent is started during an acute phase (e.g., immediately after onset or within 12 hours after onset) of a nervous system disease such as nerve injury (preferably spinal cord injury). The onset is a time when a symptom of a disease or a factor directly causing the disease can be recognized. For example, in nerve injury such as spinal cord injury, the onset is a time at which a nerve is injured.

EXAMPLES

The present invention will be described in detail below based on examples, but the present invention is not limited by the examples.

Example 1. Apoptosis Inhibiting Effect on Cerebral Cortical Neurons

The apoptosis inhibiting effect of methylcobalamin on cerebral cortical neurons was examined by TUNEL assay. Specifically, the examination was carried out as follows.

Example 1-1. Preparation of Cerebral Cortical Neurons

Cerebral cortical neurons were collected and cultured by a conventional method. Cerebral cortex was dissected from a fetus of a Sprague-Dawley (SD) rat (18th day of pregnancy) and recovered in ice-cooled Dulbecco's Modified Eagle Medium (DMEM) containing 10% fetal bovine serum (FBS) and 1% penicillin/streptomycin. The pia mater and blood vessels were removed, and the remaining cerebral cortex was transferred to DMEM (containing 1% penicillin/streptomycin and no FBS) and cut into small pieces having a size of 1 mm by surgical scissors. Papain (final concentration, 2 mg/ml) was added to the cell mixture, and the mixture was allowed to react at 37° C. for 30 minutes. DNase I (70 U/ml) was added to the reaction mixture and reaction was carried out for 30 seconds. Then, DMEM containing 10% FBS and 1% penicillin/streptomycin was added to terminate the reaction. The cell mixture was centrifuged at 800 rpm, the residue was re-suspended in DMEM containing 10% FBS and 1% penicillin/streptomycin, and the suspension was seeded on a dish coated with poly-L lysine (PLL). At 4 hours after the cell seeding, the medium was replaced with Neurobasal medium (containing 10% B27 supplement and 1% penicillin/streptomycin).

Example 1-2. TUNEL Assay

To the cerebral cortical neurons (Example 1-1) cultured on a PLL-coated 8-well chamber slide, 20 mM glutamic acid and 10 μM methylcobalamin (MeCbl) were added. After 18 hours, the proportion of apoptotic cells was evaluated using Promega's DeadEnd Fluorometric TUNEL System. Cells were fixed with 4% paraformaldehyde (PFA) at 4° C. for 25 minutes. After cells were permeabilized with 0.2% Triton X-100 for 5 minutes, an incubation buffer was added, and the mixture was left stand at 37° C. with light shielding for 60 minutes to label the permeabilized cells. The nuclei were labeled with 4'6-diamidino-2-phenylindole (DAPI). The total cell number and the number of TUNEL-positive cells were determined.

Example 1-3. Results

The results are shown in FIG. 1. The values corresponding to data in the graph of FIG. 1 are shown in Table 1. In the TUNEL assay, when methylcobalamin was added alone, the proportion of apoptotic cells (%) was similar to that in the control. When glutamic acid was added alone, the proportion of apoptotic cells was significantly increased. However, when methylcobalamin was added together with glutamic acid, the proportion of apoptotic cells was significantly decreased to the level of the control.

TABLE 1

| | | | | |
|---|---|---|---|---|
| Glutamate | − | − | + | + |
| MeCbl | − | + | − | + |
| Average | 6.0 | 5.9 | 15.0 | 5.6 |
| Standard error | 1.2 | 1.3 | 1.3 | 0.6 |
| Standard deviation | 2.0 | 2.2 | 2.2 | 1.1 |

Example 2. Necrosis Inhibiting Effect on Cerebral Cortical Neurons

A necrosis inhibiting effect of methylcobalamin on cerebral cortical neurons was examined by LDH assay. Specifically, the examination was carried out as follows.

Example 2-1. LDH Assay

To the cerebral cortical neurons (Example 1-1) cultured on a PLL-coated 6-well chamber slide, 10 µM methylcobalamin was added at 30 minutes before exposure to oxygen-glucose deprivation (OGD) stress. N-methyl-D-aspartic acid (NMDA) was added to a high control as a reference. The medium was replaced with Earle's balanced salt solution (EBSS), and the neurons were exposed to the OGD stress in an atmosphere with an oxygen concentration of 1% for 3 hours. The neurons were returned to a normal medium and an atmosphere with a normal oxygen concentration. After 24 hours, the supernatant was collected, and LDH activity was measured using Cytotoxicity Detection Kit$^{PLUS}$ (SIGMA). LDH activities of the control group and the methylcobalamin addition group were calculated as proportions (%) with respect to the LDH activity of the high control.

Example 2-2. Results

The results are shown in FIG. 2. The values corresponding to data in the graph of FIG. 2 are shown in Table 2. In the LDH assay under OGD stress, the proportion of LDH activity in the methylcobalamin addition group with respect to the high control was significantly decreased as compared with that in the control group.

TABLE 2

| | MeCbl(−) | MeCbl(+) |
|---|---|---|
| Average | 3.1 | 1.3 |
| Standard error | 0.6 | 0.5 |
| Standard deviation | 1.0 | 0.8 |

Example 3. Axon Outgrowth Promoting Effect on Cerebral Cortical Neurons

An axon outgrowth promoting effect of methylcobalamin on cerebral cortical neurons was examined by a neurite outgrowth assay. Specifically, the examination was carried out as follows.

Example 3-1. Neurite Extension Assay

The cerebral cortical neurons (Example 1-1) were seeded, and the drug was added in different concentrations at 24 hours. The concentrations of methylcobalamin added were 1, 10, and 100 nM and 1, 10, and 100 µM. At 72 hours after the cell seeding, immunofluorescent staining was performed using an anti-TuJ1 antibody, and the lengths of axons (the longest neurite length per neuron) were measured. The measurement was performed on cells that were not in contact with other cells. In each evaluation, at least 30 neural axons were measured, and the mean of the obtained values was calculated and designated as a measured value.

Example 3-2. Results

The results are shown in FIG. 3. The values corresponding to data in the graph of FIG. 3 are shown in Table 3. The results of the neurite outgrowth assay showed trends for promotion of axon outgrowth dependent on the concentration, with a peak at a methylcobalamin concentration of 10 µM. At 1 and 10 µM concentrations, the axon outgrowth was significantly promoted as compared with the control group containing no drug.

TABLE 3

| | CTR | 1 nM | 10 nM | 100 nM | 1 µM | 10 µM | 100 µM |
|---|---|---|---|---|---|---|---|
| Average | 64.8 | 67.2 | 71.2 | 75.2 | 79.9 | 86.4 | 66.2 |
| Standard error | 2.9 | 3.1 | 2.3 | 2.8 | 1.6 | 4.1 | 2.2 |
| Standard deviation | 6.6 | 7.0 | 5.2 | 6.4 | 3.5 | 9.1 | 4.9 |

Example 4. Brain Ischemic Lesion Volume Reducing Effect

A brain ischemic lesion volume reducing effect of methylcobalamin was examined using a 2,3,5-triphenyltetrazolium chloride (TTC) staining method. Specifically, the examination was carried out as follows.

Example 4-1. Construction of Transient Middle Cerebral Artery Occlusion (tMCAO) Model and Administration of Drug Eight- to 9-week-old male C57BL/6J mice (about 24 g) were used. A probe for a laser Doppler blood flow meter was placed on the right skull such that blood flow in the middle cerebral artery could be monitored. The right cervical region was cut and opened, and the external carotid artery was ligated. Then, the common carotid artery was cut, and a nylon thread was inserted into the common carotid artery, and the tip was advanced while the blood flow was checked using a blood flow monitor. When the tip reached the bifurcation of the middle cerebral artery and a decrease in blood flow was observed, this state was held for 1 hour at a rectal temperature of 37° C. Then, the nylon thread was removed, and the common carotid artery was ligated. In order to administer methylcobalamin continuously, an osmotic minipump was placed and left in the dorsal subcutaneous space. After the model had been constructed, methylcobalamin was administered at a dose of 1 mg/kg/day. In an untreated group, physiological saline was administered instead of methylcobalamin according to the same procedure. After the surgery, the temperature was maintained with a rectal temperature of 37° C. until the mouse recovered from anesthesia.

Example 4-2. TTC Staining Method

At 2 days after the surgery, the mouse (Example 4-1) was sacrificed, and the cerebrum was excised. The cerebrum was cut at intervals of 1 mm to prepare coronal sections, and the sectioned slices were immersed in 2% TTC solution for 30 minutes. Images were obtained by a stereoscopic microscope, the ischemic lesion area in each slice was calculated, and all ischemic lesion areas of the cerebrum slices were summed up to calculate an ischemic lesion volume. The ischemic lesion area in each slice was calculated by the following formula: Area of unaffected hemisphere—area of affected side intact portion.

Example 4-3. Results

The results are shown in FIG. 4. The values corresponding to data in the graph of FIG. 4 are shown in Table 4. At 2 days after the tMCAO surgery, the brain ischemic lesion volume was evaluated using TTC staining. In the methylcobalamin treatment group, the ischemic lesion volume was significantly reduced by about ½ as compared with the control group.

TABLE 4

|  | Control | MeCbl |
|---|---|---|
| Average | 59.1 | 28.8 |
| Standard error | 8.0 | 3.2 |
| Standard deviation | 22.6 | 9.0 |

Example 5. M2 Macrophage Induction Promoting Effect and M1 Macrophage Induction Inhibiting Effect An M2 macrophage induction promoting effect and an M1 macrophage induction inhibiting effect of methylcobalamin were examined by a Western blot method and an immunohistological evaluation method. Specifically, the examination was carried out as follows.

Example 5-1. Preparation of Macrophage Cell Line

Mouse macrophage cell line J774A.1 (JCRB9108) was purchased from JCRB Cell Bank (Laboratory of Cell Cultures), Osaka, Japan. Cells were cultured in DMEM containing 10% FBS and 1% penicillin/streptomycin.

Example 5-2. Western Blot

The J774A.1 cells (Example 5-1) were seeded on a dish having a diameter of 6 cm. After 4 days, proteins were collected using a cell lysis buffer containing a cocktail of protease inhibitors. The protein concentration was measured by BCA assay. Then, 50 µg of each sample was subjected to SDS-PAGE, and the electrophoresed proteins were transferred to a polyvinylidene difluoride membrane. The membrane was blocked with a blocking buffer for 1 hour, and then the proteins were allowed to react with primary antibodies at 4° C. overnight. The proteins were further allowed to react with a secondary antibody at room temperature for 1 hour and detected using ECL Western Blotting Detection System. To detect the M1 markers iNOS and IL-1β, lipopolysaccharide (LPS) (100 ng/ml) and methylcobalamin were added at 24 hours before collecting the proteins. To detect the M2 markers Arg1 and CD206, IL-4 (20 ng/ml) and methylcobalamin were added at 72 hours before collecting the proteins.

The primary antibodies used were a rabbit anti-IL-1β polyclonal antibody (Santa Cruz), a rabbit anti-iNOS monoclonal antibody (Abcam), a rabbit anti-Arg1 polyclonal antibody (Santa Cruz), and a rabbit anti-CD206 monoclonal antibody (Abcam). The secondary antibody used was anti-rabbit IgG, horseradish peroxidase-linked whole antibody from donkey (GE Healthcare Life Sciences).

Example 5-3. Method for Immunohistological Evaluation

The J774A.1 cells (Example 5-1) were seeded on a dish having a diameter of 6 cm. After 4 days, cells were fixed with 4% PFA for 20 minutes. Blocking was performed for 30 minutes, and the cells were allowed to react with primary antibodies at 4° C. overnight. The cells were further allowed to react with a secondary antibody at room temperature for 1 hour so that the nuclei were labeled with DAPI. To detect the M1 marker iNOS, LPS (100 ng/ml) and methylcobalamin were added at 24 hours before fixing the cells. To detect the M2 marker Arg1, IL-4 (20 ng/ml) and methylcobalamin were added at 72 hours before fixing the cells.

The primary antibodies used were a rabbit anti-iNOS monoclonal antibody (Abcam) and a rabbit anti-Arg1 polyclonal antibody (Santa Cruz). The secondary antibody used was an Alexa 488-labeled goat anti-rabbit IgG antibody (Life Technologies) or an Alexa 568-labeled goat anti-rabbit IgG antibody (Life Technologies).

Example 5-4. Results

The results of Western blot are shown in FIGS. 5 and 6. The values corresponding to data in the graphs of FIG. 5 are shown in Table 5, and the values corresponding to data in the graphs of FIG. 6 are shown in Table 6. The M1 marker levels were as follows: As compared with LPS alone, the IL-1β level was significantly decreased when 100 nM methylcobalamin was added in combination, and the iNOS level was significantly decreased when 100 nM to 10 µM methylcobalamin was added in combination. As compared with IL-4 alone, the level of the M2 marker Arg1 was significantly increased when 100 nM and 1 µM methylcobalamin was added in combination. Peaks of the CD206 levels were observed when methylcobalamin was added at 100 nM to 1 µM.

TABLE 5

|  |  | LPS | − | + | + | + | + | + | + | + | + |
|---|---|---|---|---|---|---|---|---|---|---|---|
|  |  | MeCbl | − | − | 1 nM | 10 nM | 100 nM | 1 µM | 10 µM | 100 µM | 1 mM |
| IL-1β | Average | | 0.01 | 1.00 | 0.91 | 0.68 | 0.46 | 0.46 | 0.60 | 0.75 | 1.26 |
|  | Standard error | | 0.00 | 0.05 | 0.14 | 0.07 | 0.07 | 0.19 | 0.24 | 0.20 | 0.04 |
|  | Standard deviation | | 0.00 | 0.09 | 0.24 | 0.11 | 0.12 | 0.34 | 0.41 | 0.35 | 0.06 |
| INOS | Average | | 0.01 | 1.00 | 0.87 | 0.56 | 0.15 | 0.27 | 0.33 | 0.45 | 0.53 |
|  | Standard error | | 0.00 | 0.12 | 0.12 | 0.11 | 0.08 | 0.04 | 0.03 | 0.12 | 0.38 |
|  | Standard deviation | | 0.00 | 0.21 | 0.21 | 0.19 | 0.13 | 0.07 | 0.04 | 0.21 | 0.65 |

TABLE 6

|  |  | − | + | + | + | + | + | + | + | + |
|---|---|---|---|---|---|---|---|---|---|---|
| IL-4 |  | − | + | + | + | + | + | + | + | + |
| MeCbl |  | − | − | 1 nM | 10 nM | 100 nM | 1 μM | 10 μM | 100 μM | 1 mM |
| Arg1 | Average | 0.02 | 1.00 | 1.42 | 1.60 | 1.93 | 1.65 | 1.26 | 0.92 | 0.54 |
|  | Standard error | 0.00 | 0.19 | 0.11 | 0.11 | 0.20 | 0.26 | 0.14 | 0.17 | 0.08 |
|  | Standard deviation | 0.00 | 0.38 | 0.21 | 0.21 | 0.40 | 0.53 | 0.28 | 0.34 | 0.17 |
| CD206 | Average | 0.02 | 1.00 | 1.28 | 1.49 | 1.53 | 1.59 | 1.08 | 1.12 | 0.78 |
|  | Standard error | 0.00 | 0.20 | 0.31 | 0.27 | 0.33 | 0.17 | 0.36 | 0.17 | 0.63 |
|  | Standard deviation | 0.00 | 0.39 | 0.62 | 0.55 | 0.66 | 0.33 | 0.73 | 0.34 | 1.25 |

The results of the immunohistological evaluation are shown in FIG. 7. The values corresponding to data in the graphs of FIG. 7 are shown in Table 7. As compared with LPS alone, the proportion of cells positive for the M1 marker iNOS was significantly decreased when 10 nM to 100 μM methylcobalamin was added in combination. As compared to IL-4 added alone, the proportion of cells positive for the M2 marker Arg1 was significantly increased when 10 nM to 1 μM methylcobalamin was added in combination.

In the immunofluorescent staining, a switch from M1 to M2 was observed with a peak around 100 nM methylcobalamin as in the above-described Western blot.

TABLE 7

|  |  | − | + | + | + | + | + | + | + | + |
|---|---|---|---|---|---|---|---|---|---|---|
| LPS |  | − | + | + | + | + | + | + | + | + |
| MeCbl |  | − | − | 1 nM | 10 nM | 100 nM | 1 μM | 10 μM | 100 μM | 1 mM |
| INOS | Average | 0.00 | 21.28 | 16.64 | 9.57 | 7.26 | 3.42 | 11.45 | 10.34 | 17.57 |
|  | Standard error | 0.00 | 1.93 | 0.63 | 0.43 | 1.01 | 0.70 | 1.42 | 2.29 | 2.22 |
|  | Standard deviation | 0.00 | 3.35 | 1.09 | 0.75 | 1.75 | 1.22 | 2.47 | 3.96 | 3.85 |
| IL-4 |  | − | + | + | + | + | + | + | + | + |
| MeCbl |  | − | − | 1 nM | 10 nM | 100 nM | 1 μM | 10 μM | 100 μM | 1 mM |
| Arg1 | Average | 1.15 | 8.22 | 10.90 | 18.57 | 18.95 | 19.32 | 15.24 | 10.61 | 9.49 |
|  | Standard error | 0.62 | 0.26 | 1.72 | 1.15 | 2.48 | 2.75 | 2.34 | 2.68 | 0.87 |
|  | Standard deviation | 1.07 | 0.45 | 2.98 | 2.00 | 4.29 | 4.77 | 4.05 | 4.64 | 1.50 |

Example 6. Analysis of Mechanism of Macrophage Induction Action

The mechanism of the macrophage induction (Example 5) by methylcobalamin was analyzed. Specifically, the analysis was carried out as follows. At 30 minutes after IL-4 and methylcobalamin (100 nM and 1 mM) were added, activation of Akt, 4EBP1, and S6K in the Akt-mTOR pathway (one of the major signaling pathways that induce M2 gene expression) was evaluated by Western blot. In the pathway, Akt phosphorylation occurs in response to an upstream signal, and 4EBP1 phosphorylation and S6K phosphorylation further occur through mTORC1 in the downstream. The S6K phosphorylation provides a negative feedback to the upstream of the signaling pathway. Western blot was performed as in Example 5-2, except that IL-4 (20 ng/ml), methylcobalamin, and RAD001 (200 nM) were added at 30 minutes before the proteins were collected, and the primary antibodies for detection were changed.

The results are shown in FIGS. 8-1, 8-2, and 8-3. The values corresponding to data in the graphs of FIGS. 8-1, 8-2, and 8-3 are shown in Table 8. When IL-4 was added, activation of Akt and both 4EBP1 and S6K in the downstream was observed. As compared with IL-4 alone, the activation of 4EBP1 and the activation of S6K were both enhanced when IL-4 and 100 nM methylcobalamin were used in combination. However, when the methylcobalamin concentration was 1 mM, the activity of Akt in the upstream was decreased although 4EBP1 and S6K were activated. When RAD001, which is an inhibitor of mTOR, was further added in addition to IL-4 and methylcobalamin, the activity of Akt in the upstream was rescued, and the activities of 4EBP1 and S6K in the downstream were suppressed. Thus, a mechanism was suggested in which the Akt activity to induce M2 gene in the upstream was suppressed by a negative feedback mechanism from the downstream when a high concentration of methylcobalamin was added.

TABLE 8

|  |  | − | + | + | + | + |
|---|---|---|---|---|---|---|
| IL-4 |  | − | + | + | + | + |
| MeCbl |  | − | − | 100 nM | 1 mM | 1 mM |
| RAD001 |  | − | − | − | − | + |
| p-Akt/ Akt | Average | 1.00 | 2.05 | 3.58 | 2.59 | 3.78 |
|  | Standard error | 0.04 | 0.14 | 0.21 | 0.19 | 0.19 |
|  | Standard deviation | 0.07 | 0.24 | 0.37 | 0.32 | 0.34 |
| p-4EBP1/ 4EBP1 | Average | 1.00 | 2.12 | 4.94 | 6.08 | 2.78 |
|  | Standard error | 0.12 | 0.37 | 0.25 | 0.34 | 0.58 |
|  | Standard deviation | 0.21 | 0.63 | 0.43 | 0.58 | 1.01 |
| p-S6K/ S6K | Average | 1.00 | 1.80 | 2.65 | 3.12 | 0.33 |
|  | Standard error | 0.15 | 0.02 | 0.06 | 0.09 | 0.13 |

TABLE 8-continued

| IL-4 | − | + | + | + | + |
|---|---|---|---|---|---|
| MeCbl | − | − | 100 nM | 1 mM | 1 mM |
| RAD001 | − | − | − | − | + |
| Standard deviation | 0.26 | 0.04 | 0.11 | 0.16 | 0.23 |

Example 7. Analysis of Macrophage Phenotypes after Sciatic Nerve Injury

Effects of methylcobalamin on macrophage phenotypes after sciatic nerve injury were analyzed by an immunohistological evaluation method. Specifically, the analysis was carried out as follows. Using transverse nerve sections at 2.5 mm in the proximal direction, at the injury site, and at 2.5, 5.0, and 7.5 mm in the distal direction, macrophages were evaluated by immunofluorescence staining at 1, 3, 7, and 14 days after sciatic nerve injury. The proximal direction refers to a cell body side of an axon with respect to an injury site, and the distal direction refers to a terminal side of an axon with respect to an injury site. Each of the distances indicates a distance from the injury site (the same applies to Example 8). Macrophages were labeled with CD68, an M1 marker iNOS, and an M2 marker CD206. The proportion of M1 macrophage was calculated by the following formula: Proportion of M1 macrophage (%)=number of M1-marker positive macrophages per $mm^2$/number of macrophages per $mm^2 \times 100$. A more detailed description will be provided below.

Example 7-1. Surgical Treatment (Rat Sciatic Nerve Crush Injury Model)

Six-week-old male Wistar rats (about 200 g) were used. The left sciatic nerve was exteriorized, and crush injury of the sciatic nerve was made on the proximal side by forceps. The nerve was crushed for 10 seconds three times at 10-second intervals. The fascia and skin were sutured using 3-0 nylon. A non-injury group which underwent only sciatic nerve exposure, an untreated group, and a methylcobalamin treatment group were compared. To administer methylcobalamin continuously, an osmotic minipump was placed and left in the dorsal subcutaneous space, and methylcobalamin was administered at a dose of 1 mg/kg/day. In an untreated group, physiological saline was administered instead of methylcobalamin according to the same procedure.

Example 7-2. Morphological and Histological Analysis

At 1, 3, 7, and 14 days after the surgery, rats were anesthetized with an anesthetic agent. The left sciatic nerve was collected, fixed with 4% PFA for 7 days and with 20% sucrose for 24 hours, and the fixed nerve was freeze-embedded. The embedded tissue was sliced into a 5-μm-thick slice in a nerve short-axis direction and placed on a glass slide. Slices were obtained from 5 positions of 2.5 mm in the proximal direction from an injured region, the injured region, and 2.5, 5.0, and 7.5 mm in the distal direction. The slices were dried for 1 hour and fixed with 95% methanol for 30 minutes. The fixed slices were blocked and allowed to react with primary antibodies at 4° C. overnight. The cells were further allowed to react with a secondary antibody at room temperature for 1 hour so that the nuclei were labeled with DAPI.

The primary antibodies used were a mouse anti-CD68 monoclonal antibody (Abcam), a rabbit anti-iNOS monoclonal antibody (Abcam), a rabbit anti-CD206 monoclonal antibody (Abcam), a rabbit anti-neurofilament 200 (NF 200) polyclonal antibody (SIGMA), and a mouse anti-myelin basic protein (MBP) monoclonal antibody (Calbiochem). The secondary antibodies used were an Alexa 488-labeled goat anti-mouse IgG antibody (Life Technologies), an Alexa 488-labeled goat anti-rabbit IgG antibody (Life Technologies), an Alexa 568-labeled goat anti-mouse IgG antibody (Life Technologies), and an Alexa 568-labeled goat anti-rabbit IgG antibody (Life Technologies).

Example 7-3. Results

The results are shown in FIGS. 9 and 10. The values corresponding to data in the graphs of FIG. 9 are shown in Tables 9-1, 9-2, and 9-3, and the values corresponding to data in the graphs of FIG. 10 are shown in Tables 10-1, 10-2, and 10-3. In the methylcobalamin treatment group, the numbers of macrophages accumulated in the injury site were significantly decreased at 3, 7, and 14 days after the surgery, as compared to the untreated group. At the distal positions, the number of macrophages was increased behind the injury site, and there was a significant difference at 14 days after the surgery.

In the methylcobalamin treatment group, the numbers of M1 macrophages were significantly decreased at all evaluation days. In the distal portions, there were significant differences at 7 and 14 days after the surgery. Similar trends were observed for the proportions of M1 macrophages.

In the methylcobalamin treatment group, the numbers of M2 macrophages were significantly increased at 1, 7 and 14 days after the surgery at the injury site. There was a significant difference at 5 mm in the distal direction at 7 days after the surgery and at 7.5 mm in the distal direction at 7 and 14 days after the surgery. Similar trends were observed for the proportions of M2 macrophage.

TABLE 9-1

| | | | Number of macrophages | | | | |
|---|---|---|---|---|---|---|---|
| | | | 2.5 mm in the proximal direction | Injury site | 2.5 mm in the distal direction | 5.0 mm in the distal direction | 7.5 mm in the distal direction |
| POD1 | CTR | Average | 40.14 | 418.55 | 75.56 | 62.20 | 45.38 |
| | | Standard error | 5.58 | 22.81 | 8.25 | 5.69 | 6.94 |
| | | Standard deviation | 13.67 | 55.87 | 20.22 | 16.38 | 16.99 |
| | MeCbl | Average | 40.53 | 335.86 | 64.37 | 43.67 | 35.68 |
| | | Standard error | 3.47 | 32.55 | 11.81 | 6.02 | 3.84 |
| | | Standard deviation | 8.50 | 79.74 | 28.92 | 14.74 | 9.42 |

TABLE 9-1-continued

| | | | \multicolumn{5}{c}{Number of macrophages} |
|---|---|---|---|---|---|---|---|
| | | | 2.5 mm in the proximal direction | Injury site | 2.5 mm in the distal direction | 5.0 mm in the distal direction | 7.5 mm in the distal direction |
| | Sham | Average | 12.56 | 17.12 | 19.41 | 18.65 | 13.70 |
| | | Standard error | 5.71 | 1.74 | 6.04 | 6.12 | 1.32 |
| | | Standard deviation | 9.99 | 3.02 | 10.46 | 10.51 | 2.28 |
| POD3 | CTR | Average | 91.25 | 1672.85 | 209.11 | 143.85 | 159.68 |
| | | Standard error | 13.14 | 125.76 | 33.95 | 28.74 | 39.69 |
| | | Standard deviation | 46.88 | 308.04 | 83.17 | 70.40 | 97.23 |
| | MeCbl | Average | 48.52 | 1261.77 | 181.38 | 135.88 | 124.33 |
| | | Standard error | 5.34 | 112.29 | 25.25 | 26.07 | 19.03 |
| | | Standard deviation | 13.07 | 275.06 | 61.85 | 63.87 | 46.63 |
| | Sham | Average | 20.55 | 22.07 | 18.65 | 16.74 | 17.12 |
| | | Standard error | 13.46 | 13.35 | 11.15 | 8.70 | 10.15 |
| | | Standard deviation | 23.31 | 23.12 | 19.32 | 15.07 | 17.57 |
| POD7 | CTR | Average | 74.92 | 1402.02 | 994.51 | 386.01 | 856.04 |
| | | Standard error | 22.81 | 45.54 | 74.84 | 154.59 | 115.89 |
| | | Standard deviation | 55.88 | 111.78 | 183.31 | 378.66 | 283.87 |
| | MeCbl | Average | 36.63 | 1096.37 | 921.92 | 763.17 | 584.14 |
| | | Standard error | 5.30 | 60.32 | 50.32 | 43.99 | 39.33 |
| | | Standard deviation | 12.98 | 147.76 | 123.26 | 122.45 | 96.33 |
| | Sham | Average | 7.51 | 7.61 | 15.50 | 11.42 | 3.51 |
| | | Standard error | 1.37 | 3.63 | 4.03 | 5.23 | 4.39 |
| | | Standard deviation | 2.38 | 6.29 | 5.96 | 3.06 | 7.60 |
| POD14 | CTR | Average | 67.04 | 1327.81 | 1447.08 | 1187.11 | 989.31 |
| | | Standard error | 27.39 | 105.88 | 102.42 | 82.54 | 70.54 |
| | | Standard deviation | 67.09 | 259.36 | 250.87 | 202.19 | 172.78 |
| | MeCbl | Average | 51.79 | 899.57 | 898.91 | 827.51 | 752.29 |
| | | Standard error | 5.77 | 50.94 | 61.50 | 50.46 | 12.32 |
| | | Standard deviation | 14.14 | 124.77 | 150.63 | 123.59 | 30.18 |
| | Sham | Average | 12.18 | 14.46 | 9.13 | 9.13 | 16.74 |
| | | Standard error | 5.53 | 5.98 | 2.38 | 2.38 | 7.72 |
| | | Standard deviation | 9.57 | 10.36 | 4.12 | 4.12 | 13.38 |

TABLE 9-2

| | | | \multicolumn{5}{c}{Number of M1 macrophages} |
|---|---|---|---|---|---|---|---|
| | | | 2.5 mm in the proximal direction | Injury site | 2.5 mm in the distal direction | 5.0 mm in the distal direction | 7.5 mm in the distal direction |
| POD1 | CTR | Average | 1.90 | 123.29 | 16.74 | 10.85 | 6.50 |
| | | Standard error | 0.70 | 21.41 | 6.37 | 4.51 | 2.15 |
| | | Standard deviation | 1.72 | 52.44 | 15.60 | 11.06 | 5.28 |
| | MeCbl | Average | 3.42 | 63.55 | 10.27 | 4.40 | 3.21 |
| | | Standard error | 0.51 | 6.55 | 2.48 | 0.64 | 1.25 |
| | | Standard deviation | 1.25 | 15.04 | 6.08 | 1.58 | 3.08 |
| | Sham | Average | 1.52 | 0.00 | 0.76 | 1.52 | 1.52 |
| | | Standard error | 1.52 | 0.00 | 0.76 | 1.52 | 0.76 |
| | | Standard deviation | 2.54 | 0.00 | 1.32 | 2.64 | 1.32 |
| POD3 | CTR | Average | 6.09 | 379.02 | 58.44 | 32.14 | 28.10 |
| | | Standard error | 0.96 | 42.23 | 17.81 | 9.07 | 7.77 |
| | | Standard deviation | 2.36 | 103.44 | 43.63 | 22.22 | 13.02 |
| | MeCbl | Average | 3.04 | 198.96 | 23.50 | 13.13 | 15.57 |
| | | Standard error | 1.13 | 33.23 | 4.12 | 3.15 | 3.19 |
| | | Standard deviation | 2.76 | 81.33 | 10.09 | 7.72 | 7.80 |
| | Sham | Average | 2.28 | 0.00 | 0.76 | 0.76 | 0.00 |
| | | Standard error | 1.32 | 0.00 | 0.76 | 0.76 | 0.00 |
| | | Standard deviation | 2.28 | 0.00 | 1.32 | 1.32 | 0.00 |
| POD7 | CTR | Average | 5.33 | 109.25 | 79.65 | 102.59 | 108.44 |
| | | Standard error | 2.51 | 19.33 | 13.48 | 14.38 | 23.24 |
| | | Standard deviation | 6.40 | 46.51 | 33.01 | 35.23 | 56.94 |
| | MeCbl | Average | 1.54 | 47.56 | 37.09 | 25.29 | 22.71 |
| | | Standard error | 0.77 | 7.92 | 8.97 | 5.44 | 2.75 |
| | | Standard deviation | 1.88 | 19.40 | 21.97 | 13.32 | 5.73 |
| | Sham | Average | 0.76 | 1.52 | 2.28 | 0.75 | 0.76 |
| | | Standard error | 0.76 | 0.76 | 1.32 | 0.76 | 0.76 |
| | | Standard deviation | 1.32 | 1.32 | 2.28 | 1.32 | 1.32 |
| POD14 | CTR | Average | 6.09 | 69.10 | 91.97 | 87.58 | 61.97 |
| | | Standard error | 2.93 | 8.70 | 8.82 | 16.23 | 13.23 |
| | | Standard deviation | 7.17 | 21.32 | 21.60 | 39.75 | 32.40 |

TABLE 9-2-continued

| | | | 2.5 mm in the proximal direction | Injury site | 2.5 mm in the distal direction | 5.0 mm in the distal direction | 7.5 mm in the distal direction |
|---|---|---|---|---|---|---|---|
| | | Number of M1 macrophages | | | | | |
| | MeCbl | Average | 2.34 | 21.33 | 27.86 | 22.35 | 15.59 |
| | | Standard error | 0.83 | 2.10 | 5.32 | 2.34 | 2.88 |
| | | Standard deviation | 2.04 | 5.14 | 13.04 | 5.72 | 7.06 |
| | Sham | Average | 0.76 | 0.76 | 0.76 | 0.76 | 0.00 |
| | | Standard error | 0.76 | 0.76 | 0.76 | 0.76 | 0.00 |
| | | Standard deviation | 1.32 | 1.32 | 1.32 | 1.32 | 0.00 |

TABLE 9-3

| | | | 2.5 mm in the proximal direction | Injury site | 2.5 mm in the distal direction | 5.0 mm in the distal direction | 7.5 mm in the distal direction |
|---|---|---|---|---|---|---|---|
| | | M1 macrophage ratio | | | | | |
| POD1 | CTR | Average | 0.084 | 0.262 | 0.183 | 0.143 | 0.152 |
| | | Standard error | 0.029 | 0.038 | 0.050 | 0.040 | 0.027 |
| | | Standard deviation | 0.071 | 0.092 | 0.121 | 0.098 | 0.066 |
| | MeCbl | Average | 0.095 | 0.195 | 0.183 | 0.109 | 0.097 |
| | | Standard error | 0.019 | 0.012 | 0.041 | 0.024 | 0.030 |
| | | Standard deviation | 0.048 | 0.030 | 0.100 | 0.058 | 0.073 |
| POD3 | CTR | Average | 0.088 | 0.226 | 0.200 | 0.192 | 0.190 |
| | | Standard error | 0.013 | 0.016 | 0.038 | 0.026 | 0.030 |
| | | Standard deviation | 0.031 | 0.040 | 0.094 | 0.064 | 0.073 |
| | MeCbl | Average | 0.068 | 0.163 | 0.165 | 0.145 | 0.186 |
| | | Standard error | 0.025 | 0.020 | 0.033 | 0.029 | 0.025 |
| | | Standard deviation | 0.061 | 0.049 | 0.081 | 0.071 | 0.061 |
| POD7 | CTR | Average | 0.085 | 0.079 | 0.080 | 0.104 | 0.126 |
| | | Standard error | 0.022 | 0.014 | 0.011 | 0.016 | 0.039 |
| | | Standard deviation | 0.054 | 0.034 | 0.026 | 0.038 | 0.096 |
| | MeCbl | Average | 0.049 | 0.046 | 0.043 | 0.039 | 0.045 |
| | | Standard error | 0.022 | 0.009 | 0.009 | 0.009 | 0.007 |
| | | Standard deviation | 0.055 | 0.022 | 0.023 | 0.022 | 0.017 |
| POD14 | CTR | Average | 0.082 | 0.051 | 0.066 | 0.077 | 0.062 |
| | | Standard error | 0.010 | 0.004 | 0.010 | 0.015 | 0.012 |
| | | Standard deviation | 0.023 | 0.011 | 0.024 | 0.036 | 0.029 |
| | MeCbl | Average | 0.039 | 0.025 | 0.033 | 0.029 | 0.024 |
| | | Standard error | 0.013 | 0.004 | 0.004 | 0.003 | 0.004 |
| | | Standard deviation | 0.031 | 0.009 | 0.009 | 0.007 | 0.009 |

TABLE 10-1

| | | | 2.5 mm in the proximal direction | Injury site | 2.5 mm in the distal direction | 5.0 mm in the distal direction | 7.5 mm in the distal direction |
|---|---|---|---|---|---|---|---|
| | | Number of macrophages | | | | | |
| POD1 | CTR | Average | 40.14 | 418.55 | 75.56 | 62.20 | 45.38 |
| | | Standard error | 5.58 | 22.81 | 8.25 | 5.59 | 6.34 |
| | | Standard deviation | 13.67 | 55.87 | 20.22 | 16.38 | 16.99 |
| | MeCbl | Average | 40.53 | 336.86 | 64.37 | 43.67 | 35.68 |
| | | Standard error | 3.47 | 32.55 | 11.81 | 6.02 | 3.84 |
| | | Standard deviation | 8.50 | 73.74 | 28.92 | 14.74 | 3.42 |
| | Sham | Average | 12.56 | 17.12 | 19.41 | 18.65 | 13.70 |
| | | Standard error | 5.71 | 1.74 | 6.04 | 6.12 | 1.32 |
| | | Standard deviation | 9.89 | 3.02 | 10.46 | 10.61 | 2.28 |
| POD3 | CTR | Average | 81.25 | 1672.85 | 208.11 | 143.85 | 158.68 |
| | | Standard error | 19.14 | 125.76 | 33.95 | 28.74 | 39.69 |
| | | Standard deviation | 46.88 | 308.04 | 83.17 | 70.40 | 97.23 |
| | MeCbl | Average | 48.52 | 1261.77 | 181.38 | 135.88 | 124.99 |
| | | Standard error | 5.34 | 112.29 | 25.25 | 26.07 | 19.00 |
| | | Standard deviation | 13.07 | 275.06 | 61.85 | 63.87 | 46.63 |

TABLE 10-1-continued

| | | | Number of macrophages | | | | |
|---|---|---|---|---|---|---|---|
| | | | 2.5 mm in the proximal direction | Injury site | 2.5 mm in the distal direction | 5.0 mm in the distal direction | 7.5 mm in the distal direction |
| | Sham | Average | 20.55 | 22.07 | 18.65 | 16.74 | 17.12 |
| | | Standard error | 13.46 | 13.35 | 11.15 | 8.70 | 10.15 |
| | | Standard deviation | 23.31 | 23.12 | 19.32 | 15.07 | 17.57 |
| POD7 | CTR | Average | 74.32 | 1402.02 | 994.51 | 986.01 | 856.04 |
| | | Standard error | 22.81 | 45.64 | 74.84 | 154.59 | 115.89 |
| | | Standard deviation | 55.88 | 111.78 | 183.31 | 378.66 | 283.87 |
| | MeCbl | Average | 36.63 | 1096.37 | 921.92 | 763.17 | 584.14 |
| | | Standard error | 5.20 | 60.32 | 50.32 | 49.99 | 39.33 |
| | | Standard deviation | 12.98 | 147.76 | 123.26 | 122.45 | 96.33 |
| | Sham | Average | 7.61 | 7.61 | 15.60 | 11.42 | 9.51 |
| | | Standard error | 1.37 | 3.63 | 4.00 | 5.23 | 4.39 |
| | | Standard deviation | 2.38 | 5.29 | 6.98 | 9.06 | 7.60 |
| POD14 | CTR | Average | 57.04 | 1327.81 | 1447.08 | 1187.11 | 989.01 |
| | | Standard error | 27.39 | 105.88 | 102.42 | 82.54 | 70.54 |
| | | Standard deviation | 57.03 | 259.35 | 250.87 | 202.19 | 172.78 |
| | MeCbl | Average | 51.79 | 999.57 | 938.81 | 827.51 | 752.29 |
| | | Standard error | 5.77 | 50.34 | 61.50 | 50.46 | 12.32 |
| | | Standard deviation | 14.14 | 124.77 | 150.63 | 123.58 | 30.18 |
| | Sham | Average | 12.18 | 14.46 | 9.13 | 3.13 | 16.74 |
| | | Standard error | 5.53 | 5.98 | 2.38 | 2.38 | 7.72 |
| | | Standard deviation | 9.57 | 10.36 | 4.12 | 4.12 | 13.38 |

TABLE 10-2

| | | | Number of M2 macrophages | | | | |
|---|---|---|---|---|---|---|---|
| | | | 2.5 mm in the proximal direction | Injury site | 2.5 mm in the distal direction | 5.0 mm in the distal direction | 7.5 mm in the distal direction |
| POD1 | CTR | Average | 38.05 | 97.45 | 49.30 | 45.86 | 27.28 |
| | | Standard error | 10.42 | 13.34 | 10.28 | 10.30 | 9.54 |
| | | Standard deviation | 25.53 | 34.14 | 25.14 | 25.22 | 23.36 |
| | MeCbl | Average | 32.83 | 138.28 | 45.53 | 33.90 | 32.83 |
| | | Standard error | 6.28 | 5.65 | 14.10 | 7.73 | 5.27 |
| | | Standard deviation | 15.39 | 13.84 | 34.53 | 18.94 | 12.91 |
| | Sham | Average | 8.37 | 7.61 | 19.79 | 11.42 | 6.85 |
| | | Standard error | 4.03 | 2.74 | 10.24 | 7.34 | 2.64 |
| | | Standard deviation | 6.69 | 4.75 | 17.73 | 12.71 | 4.57 |
| POD3 | CTR | Average | 54.73 | 542.53 | 99.63 | 96.94 | 112.25 |
| | | Standard error | 15.76 | 64.42 | 28.47 | 19.34 | 35.57 |
| | | Standard deviation | 38.61 | 157.80 | 69.75 | 71.89 | 87.36 |
| | MeCbl | Average | 43.76 | 600.12 | 147.74 | 117.16 | 114.48 |
| | | Standard error | 9.59 | 45.84 | 25.64 | 26.59 | 23.23 |
| | | Standard deviation | 23.48 | 112.28 | 62.80 | 65.12 | 57.06 |
| | Sham | Average | 8.37 | 7.61 | 9.89 | 8.37 | 5.85 |
| | | Standard error | 7.26 | 5.33 | 5.49 | 4.53 | 2.64 |
| | | Standard deviation | 12.57 | 9.23 | 8.51 | 8.02 | 4.57 |
| POD7 | CTR | Average | 31.83 | 489.91 | 339.75 | 320.70 | 252.81 |
| | | Standard error | 10.84 | 36.40 | 46.66 | 13.69 | 14.25 |
| | | Standard deviation | 26.56 | 89.17 | 113.50 | 33.53 | 34.91 |
| | MeCbl | Average | 26.25 | 654.63 | 457.16 | 432.13 | 327.16 |
| | | Standard error | 8.06 | 51.64 | 21.88 | 39.46 | 21.91 |
| | | Standard deviation | 19.73 | 126.49 | 53.60 | 36.66 | 53.66 |
| | Sham | Average | 3.81 | 4.57 | 6.85 | 6.08 | 6.09 |
| | | Standard error | 2.01 | 3.49 | 3.95 | 6.08 | 3.81 |
| | | Standard deviation | 3.49 | 6.04 | 6.85 | 10.55 | 6.59 |
| POD14 | CTR | Average | 29.13 | 303.34 | 303.53 | 343.53 | 274.42 |
| | | Standard error | 8.77 | 55.74 | 54.74 | 53.15 | 33.10 |
| | | Standard deviation | 21.49 | 136.52 | 134.08 | 130.20 | 81.07 |
| | MeCbl | Average | 35.65 | 550.45 | 443.91 | 434.68 | 417.63 |
| | | Standard error | 6.13 | 36.00 | 46.74 | 49.13 | 26.20 |
| | | Standard deviation | 15.02 | 88.13 | 114.50 | 120.35 | 64.18 |
| | Sham | Average | 6.08 | 4.57 | 7.61 | 5.33 | 12.18 |
| | | Standard error | 4.03 | 3.49 | 1.52 | 2.74 | 7.61 |
| | | Standard deviation | 6.98 | 6.04 | 2.64 | 4.75 | 13.18 |

TABLE 10-3

| | | | 2.5 mm in the proximal direction | Injury site | 2.5 mm in the distal direction | 5.0 mm in the distal direction | 7.5 mm in the distal direction |
|---|---|---|---|---|---|---|---|
| POD1 | CTR | Average | 0.678 | 0.267 | 0.624 | 0.716 | 0.705 |
| | | Standard error | 0.063 | 0.026 | 0.033 | 0.035 | 0.057 |
| | | Standard deviation | 0.153 | 0.063 | 0.081 | 0.087 | 0.139 |
| | MeCbl | Average | 0.743 | 0.431 | 0.658 | 0.765 | 0.777 |
| | | Standard error | 0.057 | 0.059 | 0.028 | 0.024 | 0.041 |
| | | Standard deviation | 0.140 | 0.130 | 0.068 | 0.060 | 0.100 |
| POD3 | CTR | Average | 0.608 | 0.320 | 0.548 | 0.704 | 0.682 |
| | | Standard error | 0.046 | 0.012 | 0.048 | 0.036 | 0.024 |
| | | Standard deviation | 0.112 | 0.030 | 0.116 | 0.089 | 0.058 |
| | MeCbl | Average | 0.708 | 0.479 | 0.693 | 0.659 | 0.694 |
| | | Standard error | 0.027 | 0.037 | 0.023 | 0.021 | 0.025 |
| | | Standard deviation | 0.066 | 0.090 | 0.055 | 0.050 | 0.062 |
| POD7 | CTR | Average | 0.408 | 0.350 | 0.399 | 0.383 | 0.370 |
| | | Standard error | 0.032 | 0.024 | 0.032 | 0.018 | 0.015 |
| | | Standard deviation | 0.079 | 0.059 | 0.079 | 0.044 | 0.036 |
| | MeCbl | Average | 0.642 | 0.571 | 0.463 | 0.505 | 0.506 |
| | | Standard error | 0.027 | 0.019 | 0.031 | 0.032 | 0.021 |
| | | Standard deviation | 0.066 | 0.047 | 0.076 | 0.079 | 0.050 |
| POD14 | CTR | Average | 0.534 | 0.249 | 0.228 | 0.289 | 0.287 |
| | | Standard error | 0.037 | 0.056 | 0.050 | 0.043 | 0.040 |
| | | Standard deviation | 0.091 | 0.138 | 0.123 | 0.107 | 0.097 |
| | MeCbl | Average | 0.698 | 0.610 | 0.459 | 0.487 | 0.487 |
| | | Standard error | 0.045 | 0.031 | 0.042 | 0.032 | 0.032 |
| | | Standard deviation | 0.110 | 0.077 | 0.102 | 0.078 | 0.078 |

Table header group: M2 macrophage ratio

Example 8. Analysis of Nerve Regeneration after Sciatic Nerve Injury

Effects of methylcobalamin on nerve regeneration after sciatic nerve injury were analyzed by an immunohistological evaluation method. Specifically, the analysis was carried out as follows. Transvers sections of an injured sciatic nerve obtained at 2 weeks after sciatic nerve injury were used for evaluation. As in the macrophage evaluation, evaluations were carried out for the sections at 2.5 mm in the proximal direction from an injury site, the injury site, and 2.5, 5.0, and 7.5 mm in the distal direction. Regenerated axons were labeled with NF 200, and myelin sheaths were labeled with MBP. The myelination rate of the regenerated axons was calculated by the following formula: Myelination rate (%)=number of myelinated axons per $mm^2$/number of axons per $mm^2 \times 100$. More specifically, the analysis was performed in the same manner as in Example 7.

The results are shown in FIG. 11. The values corresponding to data in the graphs of FIG. 11 are shown in Tables 11-1, 11-2, and 11-3. In the methylcobalamin treatment group, the numbers of axons and the numbers of myelinated axons were significantly improved at the injury site. There were significant differences in the numbers of axons at 5.0 and 7.5 mm in the distal direction, in the number of myelinated axons at 2.5, 5.0, and 7.5 mm in the distal direction, and in the myelination rate at 5.0 and 7.5 mm in the distal direction. These results and the results in Example 7 indicated that methylcobalamin promotes nerve regeneration in an anti-inflammatory manner by decreasing M1 macrophages and increasing M2 macrophages in an actual nerve regeneration process.

TABLE 11-1

| | | | 2.5 mm in the proximal direction | Injury site | 2.5 mm in the distal direction | 5.0 mm in the distal direction | 7.5 mm in the distal direction |
|---|---|---|---|---|---|---|---|
| POD14 | CTR | Average | 17797 | 11202 | 13130 | 11130 | 9278 |
| | | Standard error | 821 | 329 | 243 | 279 | 306 |
| | | Standard deviation | 2010 | 805 | 596 | 684 | 750 |
| | MeCbl | Average | 16251 | 14210 | 14478 | 16663 | 14678 |
| | | Standard error | 783 | 843 | 500 | 945 | 666 |
| | | Standard deviation | 1917 | 2064 | 1224 | 2316 | 1632 |
| | Sham | Average | 17432 | 18923 | 18137 | 19267 | 19455 |
| | | Standard error | 649 | 472 | 434 | 22 | 670 |
| | | Standard deviation | 1123 | 818 | 751 | 38 | 1160 |

Table header group: Number of axons

TABLE 11-2

| | | | Number of myelinated axons | | | | |
|---|---|---|---|---|---|---|---|
| | | | 2.5 mm in the proximal direction | Injury site | 2.5 mm in the distal direction | 5.0 mm in the distal direction | 7.5 mm in the distal direction |
| POD14 | CTR | Average | 17263 | 6601 | 5257 | 1306 | 608 |
| | | Standard error | 767 | 470 | 383 | 244 | 66 |
| | | Standard deviation | 1879 | 1150 | 938 | 599 | 162 |
| | MeCbl | Average | 15838 | 9785 | 7620 | 4400 | 2473 |
| | | Standard error | 767 | 748 | 869 | 1139 | 596 |
| | | Standard deviation | 1878 | 1832 | 2128 | 2789 | 1461 |
| | Sham | Average | 17019 | 18377 | 17663 | 18698 | 18815 |
| | | Standard error | 655 | 475 | 422 | 19 | 626 |
| | | Standard deviation | 1135 | 824 | 731 | 32 | 1084 |

TABLE 11-3

| | | | Myelination ratio | | | | |
|---|---|---|---|---|---|---|---|
| | | | 2.5 mm in the proximal direction | Injury site | 2.5 mm in the distal direction | 5.0 mm in the distal direction | 7 5 mm in the distal direction |
| POD14 | CTR | Average | 0.971 | 0.592 | 0.401 | 0.118 | 0.066 |
| | | Standard error | 0.007 | 0.045 | 0.029 | 0.022 | 0.008 |
| | | Standard deviation | 0.016 | 0.111 | 0.071 | 0.055 | 0.020 |
| | MeCbl | Average | 0.975 | 0.691 | 0.531 | 0.253 | 0.163 |
| | | Standard error | 0.002 | 0.042 | 0.064 | 0.055 | 0.033 |
| | | Standard deviation | 0.005 | 0.104 | 0.156 | 0.135 | 0.080 |
| | Sham | Average | 0.976 | 0.971 | 0.974 | 0.970 | 0.967 |
| | | Standard error | 0.004 | 0.001 | 0.002 | 0.002 | 0.003 |
| | | Standard deviation | 0.006 | 0.002 | 0.003 | 0.003 | 0.005 |

Example 9. Therapeutic Effect on Spinal Cord Injury

Therapeutic effects of methylcobalamin on spinal cord injury were examined by Basso-Beattie-Bresnahan (BBB) score and thermal algesimetry test. Specifically, the examination was carried out as follows.

Example 9-1. Construction of Rat Spinal Cord Injury Model (Lateral Hemisection Model) and Drug Administration Six-week-old female Wistar rats were used. The rats were purchased from Charles River Laboratories Japan, Inc. (Yokohama, Japan). Anesthesia was performed as follows. A 1:10 dilution of a mixture of three anesthetic agents in physiological saline was administered by intraperitoneal injection. One dose consisted of 0.2 mg/kg of midazolam, 0.015 mg/kg of medetomidine, and 0.25 mg/kg of butorphanol. The rat was placed in a prone position on an operating table, and a dorsal midline incision was made. The T10 vertebral arch was removed to expose the posterior face of the spinal cord, and the left spinal cord was hemisected using a sharp-pointed surgical scalpel (spitz mess). The skin was sutured using a 4-0 nylon thread and the surgery was completed. A comparison was made among three groups: a methylcobalamin treatment group, an untreated group, and a sham group. Immediately after the surgical operation, an osmotic minipump filled with methylcobalamin (1 mg/kg/day) or physiological saline was placed for the methylcobalamin treatment group and the untreated group, respectively, and left in the left dorsal subcutaneous space. The sham group underwent only resection of the Th10 vertebral arch.

Example 9-2. Measurement of BBB Score

Each rat was separately accommodated in a cage, allowed to walk freely, and observed for 5 minutes. According to a conventional method, left-lower-extremity function was evaluated using scores of 0 (no locomotion) to 21 (normal locomotion). The evaluations were performed before surgery, and at 1, 7, 14, 21, and 28 days after the surgery.

Example 9-3. Thermal Algesimetry Test

Each rat was separately accommodated in a dedicated cage, an infrared thermal stimulation was applied to the right sole, and time until the rat retracted the hind limb was measured. To avoid damage to the skin, the stimulation was continued for 15 seconds at the maximum. The evaluations were performed before surgery, and at 7, 14, 21, and 28 days after the surgery.

Example 9-4. Results

BBB scores are shown in FIG. 12. The values corresponding to data in the graph of FIG. 12 are shown in Table 12. As compared to the untreated group, the left-lower-extremity motor function was significantly improved in the methylcobalamin administration group at 14, 21, and 28 days after the surgery.

TABLE 12

BBB score

| | | Number of days elapsed after a surgery | | | | | |
|---|---|---|---|---|---|---|---|
| | | 0 | 1 | 7 | 14 | 21 | 28 |
| CTR | Average | 21 | 0 | 3.17 | 9 | 10.33 | 10.5 |
| | Standard error | 0 | 0 | 1.64 | 2.42 | 2.80 | 2.86 |
| | Standard deviation | 0 | 0 | 4.02 | 5.93 | 6.86 | 7.01 |
| MeCbl | Average | 21 | 0.17 | 8.33 | 15.50 | 16.33 | 17 |
| | Standard error | 0 | 0.17 | 2.20 | 0.67 | 0.67 | 0.58 |
| | Standard deviation | 0 | 0.41 | 5.39 | 1.64 | 1.63 | 1.41 |
| Sham | Average | 21 | 20.8 | 21 | 21 | 21 | 21 |
| | Standard error | 0 | 0.2 | 0 | 0 | 0 | 0 |
| | Standard deviation | 0 | 0.45 | 0 | 0 | 0 | 0 |

The results of the thermal algesimetry test are shown in FIG. 13. The values corresponding to data in the graph of FIG. 13 are shown in Table 13. In the methylcobalamin treatment group, the right-lower-extremity hyperesthesia was significantly improved at 21 and 28 days after the surgery.

TABLE 13

Thermal algesimetry test
Time after spying infrared thermal stimulation

| | | Number of days elapsed after a surgery | | | | |
|---|---|---|---|---|---|---|
| | | 0 | 7 | 14 | 21 | 28 |
| CTR | Average | 9.85 | 6.64 | 7.26 | 6.97 | 7.54 |
| | Standard error | 0.37 | 0.33 | 0.41 | 0.37 | 0.26 |
| | Standard deviation | 0.91 | 0.82 | 1.01 | 0.90 | 0.64 |
| MeCbl | Average | 9.99 | 8.59 | 8.86 | 9.61 | 9.92 |
| | Standard error | 0.48 | 0.55 | 0.53 | 0.40 | 0.34 |
| | Standard deviation | 1.18 | 1.36 | 1.30 | 0.99 | 0.84 |

TABLE 13-continued

Thermal algesimetry test
Time after spying infrared thermal stimulation

| | | Number of days elapsed after a surgery | | | | |
|---|---|---|---|---|---|---|
| | | 0 | 7 | 14 | 21 | 28 |
| Sham | Average | 9.87 | 9.62 | 9.41 | 9.75 | 9.50 |
| | Standard error | 0.48 | 0.21 | 0.23 | 0.14 | 0.22 |
| | Standard deviation | 1.07 | 0.47 | 0.51 | 0.32 | 0.49 |

Example 10. M2 Microglia Induction Promoting Effect and M1 Microglia Induction Inhibiting Effect An M2 microglia induction promoting effect and an M1 microglia induction inhibiting effect of methylcobalamin were examined by a Western blot method. Specifically, the examination was carried out as follows.

Example 10-1. Western Blot

To a microglia cell line (6-3 cells), LPS (100 ng/ml) and an anti-inflammatory cytokine IL-4 (20 ng/ml) were added. Methylcobalamin solutions each having a different concentration ranging from 1 nM to 1 mM were added to the mixture, and proteins were recovered from each mixture at 1 and 3 days after the addition. Electrophoresis and transfer to a membrane were performed, the membrane was blocked, and the cells were allowed to react with each of primary antibodies against M1 markers (iNOS and IL-1β) and M2 markers (Arg1 and CD206) at 4° C. overnight. Cells were allowed to react with a secondary antibody at room temperature for 1 hour, and bands were detected using a detector.

The primary antibodies used were an anti-iNOS antibody, an anti-IL-1β antibody, an anti-Arg1 antibody, and an anti-CD206 (a mannose receptor) antibody. The secondary antibody used was an Anti-Rabbit IgG, HRP-Linked Whole Ab Sheep.

Example 10-2. Results

The results of Western blot are shown in FIGS. 14 to 15. The values corresponding to data in the graphs of FIG. 14 are shown in Table 14, and the values corresponding to data in the graphs of FIG. 15 are shown in Table 15. The amounts of pro-inflammatory (M1) markers of microglia were as follows: as compared with the case LPS alone, the amount of IL-1β protein was significantly decreased when at least 1 µM methylcobalamin was added in combination, and the amount of iNOS protein was significantly decreased when at least 10 nM methylcobalamin was added in combination. The amounts of anti-inflammatory (M2) markers were as follows: as compared with IL-4 alone, the amount of Arg1 protein was significantly increased when 1 nM to 10 µM methylcobalamin was added in combination. The amount of CD206 was significantly increased when 10 nM to 100 nM methylcobalamin was added in combination.

TABLE 14

| | | LPS | − | + | + | + | + | + | + | + | + |
|---|---|---|---|---|---|---|---|---|---|---|---|
| | | MeCbl | − | − | 1 nM | 10 nM | 100 nM | 1 μM | 10 μM | 100 μM | 1 mM |
| IL-1β | Average | | 0.06 | 1.00 | 1.02 | 0.95 | 0.83 | 0.72 | 0.58 | 0.53 | 0.32 |
| | Standard error | | 0.01 | 0.06 | 0.06 | 0.04 | 0.04 | 0.06 | 0.09 | 0.06 | 0.04 |
| | Standard deviation | | 0.01 | 0.10 | 0.11 | 0.07 | 0.06 | 0.10 | 0.10 | 0.10 | 0.06 |
| INOS | Average | | 0.17 | 1.00 | 0.87 | 0.74 | 0.76 | 0.61 | 0.46 | 0.36 | 0.05 |
| | Standard error | | 0.09 | 0.10 | 0.02 | 0.04 | 0.02 | 0.06 | 0.07 | 0.04 | 0.04 |
| | Standard deviation | | 0.15 | 0.17 | 0.03 | 0.07 | 0.03 | 0.10 | 0.13 | 0.07 | 0.06 |

TABLE 15

| | | IL-4 | − | + | + | + | + | + | + | + | + |
|---|---|---|---|---|---|---|---|---|---|---|---|
| | | MeCbl | − | − | 1 nM | 10 nM | 100 nM | 1 μM | 10 μM | 100 μM | 1 mM |
| Arg1 | Average | | 0.13 | 1.00 | 1.78 | 2.03 | 2.72 | 2.20 | 2.08 | 1.37 | 0.59 |
| | Standard error | | 0.04 | 0.19 | 0.30 | 0.13 | 0.10 | 0.08 | 0.02 | 0.13 | 0.20 |
| | Standard deviation | | 0.06 | 0.32 | 0.52 | 0.23 | 0.18 | 0.14 | 0.04 | 0.22 | 0.34 |
| CD206 | Average | | 0.63 | 1.00 | 1.11 | 1.42 | 1.39 | 1.17 | 1.17 | 1.24 | 1.11 |
| | Standard error | | 0.01 | 0.06 | 0.05 | 0.03 | 0.11 | 0.01 | 0.06 | 0.19 | 0.07 |
| | Standard deviation | | 0.02 | 0.10 | 0.09 | 0.05 | 0.19 | 0.01 | 0.10 | 0.33 | 0.12 |

Example 11. M2 Macrophage Induction Promoting Effect and M1 Macrophage Induction Inhibiting Effect An M2 macrophage induction promoting effect and an M1 macrophage induction inhibiting effect of methylcobalamin were examined. Specifically, the examination was carried out as follows.

Example 11-1. Immunofluorescent Staining

The rat spinal cord injury model of Example 9-1 was used. At 7, 14, and 28 days after the surgery, the rats were anesthetized with an anesthetic agent, and perfusion fixation was performed with 4% PFA. Then, the spinal cord including the injury site was collected and fixed with 20% sucrose for 24 hours, and the fixed spinal cord was freeze-embedded. The embedded tissue was sliced into a 5-μm-thick slice in a nerve short-axis direction and placed on a glass slide. The slice was dried for 1 hour and fixed with 100% methanol for 30 minutes. The fixed slices were blocked, and cells were allowed to react with primary antibodies at 4° C. overnight. The cells were further allowed to react with a secondary antibody at room temperature for 1 hour so that the nuclei were labeled with DAPI.

Using transverse spinal cord sections on the affected side at 2 and 1 mm on the head side and at 1 and 2 mm on the tail side from the injury site, the number of macrophages, the number of M1 (pro-inflammatory type) macrophages, the proportion of M1 macrophages, the number of M2 (anti-inflammatory type) macrophages, and the proportion of M2 macrophage per unit area, as well as the M1/M2 ratio were measured and calculated.

The primary antibodies used were an anti-CD68 antibody, an anti-iNOS antibody, and an anti-Arg1 antibody. The secondary antibodies used were an Alexa 488-labeled goat anti-rabbit IgG antibody and an Alexa 568-labeled goat anti-mouse IgG antibody.

Example 11-2. Results

The results of the immunofluorescent staining are shown in FIGS. 16 to 22. FIGS. 16 to 18 show differences in the number of macrophages, the number of M1 (pro-inflammatory type) macrophages, the proportion of M1 macrophages, the number of M2 (anti-inflammatory type) macrophages, and the proportion of M2 macrophages per unit area for each position. FIGS. 19 to 20 show changes with time in days after the surgery. FIG. 21 shows changes in the M1/M2 ratio with time in days after the surgery. FIG. 22 shows changes at each position. The values corresponding to data in the graphs of FIGS. 16 to 18 are shown in Tables 16 to 18, respectively, and the values corresponding to data in the graphs of FIG. 22 are shown in Table 19.

In the methylcobalamin treatment group, there were trends for a smaller number of accumulated macrophages per unit area as compared with the untreated group. Further, in view of the phenotypes of the macrophages, there were trends for decreased M1 macrophages and increased M2 macrophages. There were significant differences in some results.

TABLE 16

|  |  | 2 mm on the head side | 1 mm on the head side | 1 mm on the tail side | 2 mm on the tail side |
| --- | --- | --- | --- | --- | --- |
| | | Number of macrophages | | | |
| CTR | Average | 301.82 | 573.09 | 736.03 | 481.80 |
| | Standard deviation | 168.61 | 167.02 | 177.69 | 186.35 |
| MeCbI | Average | 143.88 | 268.62 | 348.57 | 155.09 |
| | Standard deviation | 54.14 | 112.44 | 101.19 | 68.10 |
| | | Number of M1 macrophages/mm2 | | | |
| CTR | Average | 65.06 | 130.79 | 166.83 | 97.60 |
| | Standard deviation | 21.26 | 32.98 | 74.57 | 40.48 |
| MeCbI | Average | 20.43 | 37.00 | 43.07 | 27.02 |
| | Standard deviation | 7.99 | 21.74 | 9.70 | 12.54 |
| | | Number of M2 macrophages/mm2 | | | |
| CTR | Average | 37.73 | 83.66 | 90.48 | 32.27 |
| | Standard deviation | 19.78 | 28.17 | 36.41 | 19.79 |
| MeCbI | Average | 25.87 | 63.85 | 76.19 | 28.76 |
| | Standard deviation | 7.71 | 27.22 | 29.22 | 11.21 |
| | | M1 macrophage ratio | | | |
| CTR | Average | 0.240 | 0.231 | 0.222 | 0.208 |
| | Standard deviation | 0.091 | 0.035 | 0.058 | 0.049 |
| MeCbI | Average | 0.143 | 0.131 | 0.129 | 0.170 |
| | Standard deviation | 0.021 | 0.032 | 0.031 | 0.025 |
| | | M2 macrophage ratio | | | |
| CTR | Average | 0.128 | 0.152 | 0.120 | 0.063 |
| | Standard deviation | 0.027 | 0.050 | 0.026 | 0.021 |
| MeCbI | Average | 0.193 | 0.242 | 0.219 | 0.194 |
| | Standard deviation | 0.068 | 0.053 | 0.045 | 0.050 |

TABLE 17

|  |  | 2 mm on the head side | 1 mm on the head side | 1 mm on the tail side | 2 mm on the tail side |
| --- | --- | --- | --- | --- | --- |
| | | Number of macrophages | | | |
| CTR | Average | 398.46 | 693.35 | 617.71 | 399.81 |
| | Standard deviation | 100.33 | 156.42 | 165.81 | 182.93 |
| MeCbI | Average | 271.15 | 362.17 | 395.70 | 254.33 |
| | Standard deviation | 163.51 | 166.70 | 146.05 | 173.16 |
| | | Number of M1 macrophages/mm2 | | | |
| CTR | Average | 53.70 | 100.09 | 95.75 | 54.77 |
| | Standard deviation | 24.77 | 29.96 | 66.00 | 55.25 |
| MeCbI | Average | 28.35 | 48.35 | 43.74 | 25.54 |
| | Standard deviation | 19.78 | 40.61 | 30.34 | 20.78 |
| | | Number of M2 macrophages/mm2 | | | |
| CTR | Average | 31.07 | 52.81 | 42.74 | 24.19 |
| | Standard deviation | 17.65 | 33.23 | 19.94 | 18.80 |
| MeCbI | Average | 36.37 | 47.90 | 43.12 | 26.29 |
| | Standard deviation | 29.10 | 32.79 | 16.99 | 7.84 |
| | | M1 macrophage ratio | | | |
| CTR | Average | 0.129 | 0.144 | 0.143 | 0.120 |
| | Standard deviation | 0.030 | 0.029 | 0.072 | 0.057 |
| MeCbI | Average | 0.103 | 0.122 | 0.102 | 0.094 |
| | Standard deviation | 0.017 | 0.050 | 0.038 | 0.020 |
| | | M2 macrophage ratio | | | |
| CTR | Average | 0.076 | 0.075 | 0.072 | 0.059 |
| | Standard deviation | 0.039 | 0.041 | 0.037 | 0.040 |
| MeCbI | Average | 0.146 | 0.130 | 0.112 | 0.143 |
| | Standard deviation | 0.080 | 0.043 | 0.034 | 0.086 |

TABLE 18

|  |  | 2 mm on the head side | 1 mm on the head side | 1 mm on the tail side | 2 mm on the tail side |
|---|---|---|---|---|---|
| Number of macrophages | | | | | |
| CTR | Average | 316.74 | 414.55 | 439.95 | 378.94 |
|  | Standard error | 26.40 | 15.21 | 31.15 | 36.07 |
|  | Standard deviation | 64.56 | 37.25 | 76.31 | 98.36 |
| MeCbI | Average | 230.75 | 320.22 | 342.11 | 245.52 |
|  | Standard error | 35.06 | 30.83 | 46.83 | 26.68 |
|  | Standard deviation | 85.83 | 75.51 | 119.60 | 65.36 |
| Number of M1 macrophages/mm2 | | | | | |
| CTR | Average | 33.93 | 51.08 | 64.79 | 50.49 |
|  | Standard error | 2.11 | 3.53 | 3.30 | 6.35 |
|  | Standard deviation | 5.16 | 8.64 | 22.77 | 15.56 |
| MeCbI | Average | 20.16 | 29.78 | 44.73 | 24.68 |
|  | Standard error | 2.95 | 6.09 | 8.34 | 6.03 |
|  | Standard deviation | 7.23 | 14.93 | 21.91 | 14.77 |
| Number of M2 macrophages/mm2 | | | | | |
| CTR | Average | 4.28 | 11.76 | 10.14 | 4.40 |
|  | Standard error | 0.83 | 2.11 | 1.43 | 0.50 |
|  | Standard deviation | 2.17 | 5.17 | 3.51 | 1.23 |
| MeCbI | Average | 7.65 | 12.98 | 10.33 | 7.42 |
|  | Standard error | 2.11 | 2.78 | 1.15 | 0.89 |
|  | Standard deviation | 5.17 | 6.81 | 2.81 | 2.19 |
| M1 macrophage ratio | | | | | |
| CTR | Average | 0.108 | 0.124 | 0.151 | 0.133 |
|  | Standard error | 0.007 | 0.008 | 0.023 | 0.007 |
|  | Standard deviation | 0.016 | 0.023 | 0.067 | 0.017 |
| MeCbI | Average | 0.089 | 0.090 | 0.132 | 0.095 |
|  | Standard error | 0.006 | 0.012 | 0.017 | 0.015 |
|  | Standard deviation | 0.013 | 0.028 | 0.042 | 0.037 |
| M2 macrophage ratio | | | | | |
| CTR | Average | 0.014 | 0.028 | 0.024 | 0.012 |
|  | Standard error | 0.004 | 0.005 | 0.004 | 0.001 |
|  | Standard deviation | 0.008 | 0.011 | 0.011 | 0.003 |
| MeCbI | Average | 0.032 | 0.039 | 0.032 | 0.032 |
|  | Standard error | 0.006 | 0.005 | 0.003 | 0.006 |
|  | Standard deviation | 0.014 | 0.013 | 0.007 | 0.014 |

TABLE 19

|  |  |  | M1/M2 | | | |
|---|---|---|---|---|---|---|
|  |  |  | 2 mm on the head side | 1 mm on the head side | 1 mm on the tail side | 2 mm on the tail side |
| 7 days after a surgery | CTR | Average | 1.98230737 | 1.737179 | 1.87175346 | 3.62357386 |
|  |  | Standard deviation | 1.01770554 | 0.8941413 | 0.44786717 | 1.63595842 |
|  | MeCbl | Average | 0.81556762 | 0.5722307 | 0.60197181 | 0.93373695 |
|  |  | Standard deviation | 0.28148608 | 0.20701435 | 0.1445533 | 0.30181695 |
| 14 days after a surgery | CTR | Average | 2.11618015 | 2.87783253 | 2.61877661 | 3.35640625 |
|  |  | Standard deviation | 1.17059363 | 2.18023676 | 1.9127902 | 3.17882907 |
|  | MeCbl | Average | 0.91059534 | 0.993049 | 0.94086406 | 0.86048838 |
|  |  | Standard deviation | 0.48325852 | 0.36363151 | 0.38103227 | 0.47425723 |
| 28 days after a surgery | CTR | Average | 11.6333333 | 5.29109347 | 7.46137087 | 11.8402778 |
|  |  | Standard deviation | 10.0675947 | 2.73818316 | 4.32116353 | 3.17208053 |
|  | MeCbl | Average | 3.35546661 | 2.45654548 | 4.29967382 | 3.54549168 |
|  |  | Standard deviation | 2.01009777 | 0.82739767 | 1.54186383 | 2.36798272 |

Example 12. Function Recovery Promoting Effect of Methylcobalamin in Photocoagulation-induced Cerebral Infarction Model Example 12-1. Subject and Method Eight to 10-week-old male C57BL/6J mice (about 24 g) were used. A photocoagulation-induced cerebral infarction model for laser light irradiation after rose bengal administration was constructed. In this model, the skull of each mouse was drilled to open a hole having a center at 2 mm from the anterior fontanel in the outward direction. At 5 minutes after a photosensitive dye rose bengal was administered, the right motor cortex as a center was irradiated with laser light to create cerebral infarction in the right lateral motor cortex. An osmotic pump (ALZET osmotic pumps, for 2-week operation) was embedded immediately after the creation of the cerebral infarction. The mice were divided into a methylcobalamin treatment group (N=3) and an untreated group (N=4), and rotarod tests (accelerating velocity method) were carried out at 2, 4, 7, 9, 11, and 14 days after the surgery creating cerebral infarction. The time until a mouse fell from a rotarod was measured, and a ratio to a maximum of 300 seconds as baseline was calculated.

Example 12-2. Results

The results are shown in FIG. 23. The value corresponding to data in the graph of FIG. 23 are shown in Table 20. At 2, 4, and 9 days after the surgery creating cerebral infarction, brain function examined in the rotarod test significantly improved in the methylcobalamin treatment group as compared with the untreated group.

TABLE 20

| | | After PIT operation | | | | | |
|---|---|---|---|---|---|---|---|
| | | 0 day | 2 days | 4 days | 7 days | 9 days | 11 days | 14 days |
| CTR | Average | 0.998 | 0.101 | 0.144 | 0.263 | 0.208 | 0.322 | 0.368 |
| | Standard deviation | 0.003 | 0.021 | 0.070 | 0.115 | 0.069 | 0.175 | 0.198 |
| MeCbl | Average | 0.998 | 0.470 | 0.573 | 0.370 | 0.437 | 0.521 | 0.510 |
| | Standard deviation | 0.004 | 0.020 | 0.048 | 0.024 | 0.155 | 0.062 | 0.017 |

The invention claimed is:

1. A method of treating a central nervous system disorder, selected from the group consisting of a cerebrovascular disorder, and central nerve injury caused by: traumatic injury, pressure from a plaster cast, electrical injury, disk herniation, or radiation exposure, the method comprising administering, to a patient with the central nervous system disorder, an agent comprising an effective amount of vitamin B12 which is at least one selected from the group consisting of methylcobalamin, cyanocobalamin, hydroxocobalamin, sulfitocobalamin, adenosylcobalamin, and salts thereof, by continuous intravenous administration for a period of time, wherein the effective amount of vitamin B12 promotes M2 macrophage/microglia induction and inhibits M1 macrophage/microglia induction.

2. The method according to claim 1, wherein the administered effective amount of the vitamin B12 administered to the patient promotes nerve regeneration in the patient.

3. The method according to claim 1, wherein the cerebrovascular disorder is at least one selected from the group consisting of cerebral infarction, cerebral hemorrhage, cerebral thrombosis, cerebral arteriosclerosis, and vascular dementia.

4. The method according to claim 1, wherein the central nerve injury is spinal cord injury.

5. The method according to claim 1, wherein the agent comprising the effective amount of the vitamin B12 is continuously administered to the patient by intravenous drip infusion.

6. The method according to claim 1, wherein the administration is started at 12 to 24 hours after onset of the central nervous system disorder.

7. The method according to claim 1, wherein the administration is started immediately after onset of the central nervous system disorder or within 12 hours of the onset.

* * * * *